(12) United States Patent
Szente Varga

(10) Patent No.: US 11,045,302 B2
(45) Date of Patent: Jun. 29, 2021

(54) VASCULAR MEDICAL DEVICE, SYSTEM AND METHOD

(71) Applicant: Swiss Capital—Engineering AG, Zürich (CH)

(72) Inventor: Michael Szente Varga, Zumikon (CH)

(73) Assignee: Swiss Capital—Engineering AG, Zürich (CH)

( * ) Notice: Subject to any disclaimer, the term of this patent is extended or adjusted under 35 U.S.C. 154(b) by 0 days.

(21) Appl. No.: 16/304,270

(22) PCT Filed: May 26, 2017

(86) PCT No.: PCT/EP2017/062809
§ 371 (c)(1),
(2) Date: Nov. 23, 2018

(87) PCT Pub. No.: WO2017/203056
PCT Pub. Date: Nov. 30, 2017

(65) Prior Publication Data
US 2019/0083229 A1    Mar. 21, 2019

Related U.S. Application Data

(63) Continuation-in-part of application No. 15/166,141, filed on May 26, 2016, now Pat. No. 10,821,009.

(30) Foreign Application Priority Data

May 26, 2016    (EP) .................................... 16171467

(51) Int. Cl.
*A61F 2/954*    (2013.01)
*A61F 2/07*    (2013.01)
(Continued)

(52) U.S. Cl.
CPC ................ *A61F 2/07* (2013.01); *A61F 2/954* (2013.01); *A61F 2/958* (2013.01); *A61F 2/97* (2013.01);
(Continued)

(58) Field of Classification Search
CPC .......... A61F 2002/061; A61F 2002/072; A61F 2002/9534; A61F 2/954; A61F 2/95;
(Continued)

(56) References Cited

U.S. PATENT DOCUMENTS 6,596,020 B2 *    7/2003    Vardi ..................... A61F 2/954
                                                       604/264
2001/0003161 A1    6/2001    Vardi et al.
(Continued)

FOREIGN PATENT DOCUMENTS

| EP | 2815722 A1 | 12/2014 |
|---|---|---|
| WO | WO2004/019823 A1 | 3/2004 |
| WO | WO2010/111666 A1 | 9/2010 |

OTHER PUBLICATIONS

WIPO, European International Preliminary Examining Authority, International Preliminary Report on Patentability dated Sep. 5, 2018 in International Patent Application No. PCT/EP2017/062809, 53 pages.
(Continued)

*Primary Examiner* — Diane D Yabut
*Assistant Examiner* — Christina C Lauer
(74) *Attorney, Agent, or Firm* — Inskeep IP Group, Inc.

(57) ABSTRACT

The present application discloses a covered stent and a method for navigating the covered stent to a branch vessel, the covered stent including a main body and at least one lateral side branch connected to the main body. A system of
(Continued)

covered stents and a method for implanting, including interconnecting the covered stents is also disclosed.

4 Claims, 17 Drawing Sheets

(51) Int. Cl.
  *A61F 2/958* (2013.01)
  *A61F 2/97* (2013.01)
  *A61F 2/06* (2013.01)
(52) U.S. Cl.
  CPC ... *A61F 2002/061* (2013.01); *A61F 2002/067* (2013.01); *A61F 2002/072* (2013.01); *A61F 2250/006* (2013.01); *A61F 2250/0098* (2013.01)
(58) Field of Classification Search
  CPC ...... A61F 2/958; A61F 2/07; A61F 2002/067; A61F 2002/0823; A61F 2/01; A61F 2/013
  See application file for complete search history.

(56) References Cited

U.S. PATENT DOCUMENTS

| | | | | |
|---|---|---|---|---|
| 2006/0184224 | A1* | 8/2006 | Angel | A61F 2/95 623/1.11 |
| 2007/0067013 | A1* | 3/2007 | Karpiel | A61F 2/954 623/1.12 |
| 2007/0112407 | A1* | 5/2007 | Mertens | A61F 2/954 623/1.11 |
| 2008/0097578 | A1 | 4/2008 | Erickson et al. | |
| 2010/0268327 | A1 | 10/2010 | Bruszewski et al. | |

OTHER PUBLICATIONS

WIPO, European International Search Authority, International Search Report and Written Opinion dated Jul. 13, 2017 in International Patent Application No. PCT/EP2017/062809, 13 pages.

The China National Intellectual Property Administration, Office Action dated Jun. 22, 2020 in Chinese Patent Application No. 201780042162.3, 21 pages.

* cited by examiner

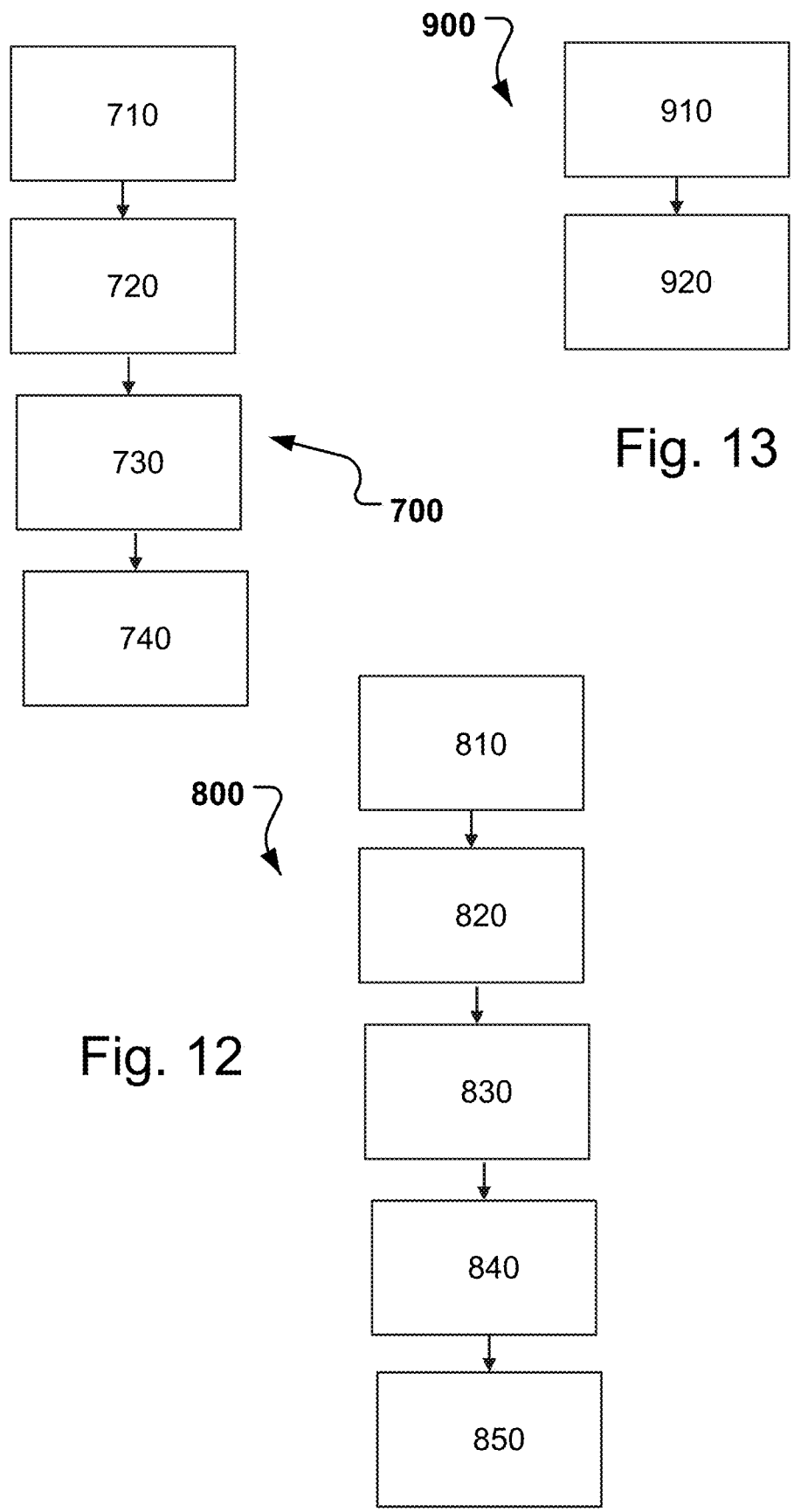

VASCULAR MEDICAL DEVICE, SYSTEM AND METHOD

RELATED APPLICATIONS

This application is the U.S. National Phase of and claims priority to International Patent Application No. PCT/EP2017/062809, International Filing Date May 26, 2017, entitled A Vascular Medical Device, System And Method; which is a continuation-in-part of and claims benefit of U.S. patent application Ser. No. 15/166,141 filed May 26, 2016 entitled A Vascular Medical Device, System And Method; and claims priority to European Application No. EP16171467.0 filed May 26, 2016 entitled A Vascular Medical Device, System And Method; all of which are incorporated herein by reference in their entireties.

BACKGROUND OF THE INVENTION

Field of the Invention

This disclosure pertains in general to the field of medical devices. More particularly the disclosure relates to a vascular medical device being a covered stent, stent graft or endoprosthesis for liquid communication with one or more side branch vessel(s), and a system of such devices, as e.g. multiple covered stents for assembly with each other, and for deployment at a target site in a patient. Also, medical procedures for deploying such devices and systems are disclosed. The target site in a patient includes for instance at least a portion of an aorta of a patient. More particularly, treatment of at least a portion of an aorta of a patient by implantation of such a device or system in a medical procedure is disclosed. The medical procedure is preferably minimally invasive vascular repair.

Description of the Prior Art

It is known to use modular covered stents or stent grafts for treatment or repair of vascular disease, such as e.g. an aneurysm. WO 2005/027784 discloses a system of modular covered stents for implantation in a diseased vessel, where the covered stents have apertures along the midsection of the covered stent. The apertures are used for aligning with branch vessels of a main vessel so that further stents can be connected at an aperture from a main vessel stent. The apertures need to be precisely aligned with the ostia of the side vessels. From the main vessel stent, a further stent graft protrudes then from each aperture into the branch vessel.

An undesired issue with such known devices is that it is difficult for the operator to correctly implant a covered stent in a main vessel aligned with branch vessels. Apertures or branches from the main vessel covered stent have to be correctly positioned in the main vessel in relation to the position of the branch vessels. The branch vessel is to be in liquid communication with the main vessel, i.e. through branch vessel covered stents or portion of a larger stent graft unit with arms to the branch vessels.

The main vessel covered stent is expanded and thus implanted in the main vessel. Once expanded and deployed, the main vessel covered stent cannot be re-positioned. Misaligned apertures or branch covered stents misaligned with branch vessels may for instance cause kinking of the branch vessel covered stent. This kinking may cause undesired reduced blood flow to the branch vessel. It may also deteriorate durability and length of life of the covered stent when implanted, caused by pulsatile flow. It may also lead to leakage, or loosening of a side branch covered stent unit from a main vessel modular covered stent.

Moreover, there is a certain risk of damaging the vessel when the operator is trying to find branch vessels using modular covered stents and in particular in case there is a certain misalignment. Prior art modular covered stents with apertures pose a further risk of damaging the vessel walls during operation since they are more or less open circular apertures facing sideways out of the modular stent. When the operator then tries to navigate such a side branch vessel into place, as described above, the open apertures may tear or otherwise damage the delicate vessel wall when being moved around inside the vessel such that the vessel wall could rupture leading to internal bleeding. This should be avoided and improved covered stents, or (modular) covered stent systems, or implantation procedures for the two latter, would be advantageous.

The aforementioned alignment challenge makes that the operation time with hitherto known devices and medical procedures becomes often very long. Long operation times increase patient risk and potential problems related to such procedures. These problems include for instance increased risk for clots occurring during the operation. Also, long operation time implies long times of X-Ray use, which both the operator and the patient are exposed to. Moreover, contrast media is then used in large amounts.

It is therefore also desired to reduce the X-Ray dosage both for the patient and operator. Shorter scanning times or less positions scanned as well as reduced use of contrast agent that needs to be injected into the patient's blood is desired. There is therefore a need to reduce time needed for such implantation procedure, both for reduction of radiation exposure of primary radiation of the patient and secondary radiation (scattered radiation) of the operator. It would be advantageous to provide a covered stent, covered stent system, or procedure to facilitate a diminished scanning time. Examples of the invention described below provide this advantage as described below.

A further undesired issue with the known art is that implantation of a covered stent implant, in particular longer endoprosthesis systems of such covered stents covering multiple side branch vessels, is a complicated operation.

In known endoprosthesis the covered stents need to be assembled in a single deployment of the covered stent system. Should for instance side branch vessel openings of a main covered stent be positioned wrongly upon deployment in relation to the side vessel, re-positioning of the main (vessel) stent is very difficult or impossible. The prior art systems allow for no flexibility or very little tolerance upon deployment regarding mal-positioning of a main stent in relation to side vessels. Flexibility of reaching side vessels with such stent is desired.

Re-positioning of further parts of a stent graft system in relation to side vessels should be advantageously provided and the deployment procedure be facilitated. Hence, a novel covered stent, covered stent system or implantation procedure is desired to allow for individual positioning of one or more side vessel stent grafts. Examples of the invention described below provide this advantage as described in more detail below.

The minimal invasive implantation of an endoprosthesis requires hitherto continuous fluoroscopic scanning by X-Ray so that the operator can see where and how to position the different covered stent modules in a patient's vascular system for assembling the endoprosthesis inside the patient.

Frequent change of scan angles of the X-Ray modality is required to enable the operator to find branch vessels in three dimensions and the relation of covered stents to apertures of a covered stent module in a main vessel. The scan techniques used for this only enables the operator to see the scanned body in one plane at a time only, i.e. in two dimensions, one layer at a time.

Three dimensional visualization of branch vessels location and orifices in relation to apertures of a covered stent requires repeatedly moving a fluoroscopy scanner arm from one plane to another plane and then moving it back again to the first plane. This is needed to ensure alignment in three dimensions between the covered stent in the main vessel and the side branch vessel. It is important that the components are placed in a correct position at the implantation site in the patient.

With multiple apertures and side branch vessel connections to be aligned for one single covered stent in the main vessel, this task becomes particularly complicated.

There is therefore a need to make the assembly less complicated. The disclosure of examples of the invention found below advantageously provides a less complicated assembly of covered stents. Reduced X-ray times and related radiation dosages would be advantageous for both patients and clinical personnel.

Thus, there is a need for a medical device and/or system, or medical procedures that are safer, avoiding the aforementioned drawbacks of known systems and procedures. Preferably a device and/or system or method is desired that makes the operation times shorter. Procedures are desired to be more easily performed by the operator. Simplified implantation procedure is desired. Complication rate is desired to be reduced. Novel medical procedures with reduced patient risk are desired. Simpler implantation is desired. Medical procedures are desired, which can be performed despite the fact that they would be avoided today in a risk assessment of patients. For instance as known stent systems would have implied too high risk for complications and open chest surgery is no option for many patients, in particular elderly patients), such simplified implantation, or devices facilitating simplified implantation, are desired. Less X-ray dosage needed during the procedure is also desired. Hence, there is a desire to be able to provide novel medical procedures, implying reduced patient risk.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing medical devices, systems, and methods according to the appended independent patent claims.

The present novel covered stent system allows, amongst others, for individual, single delivery of side vessel stent branches. This reduces total operation time considerably. Also, patient safety is improved as time is reduced and/or other side vessels still are perfused when one side vessel stent is deployed by the operator.

The novel system allows for novel medical procedures, which today would imply too high risk for the patient. Thanks to the more simple implantation, medical procedures can be performed which were avoided today in a risk assessment of patients—for instance as known stent systems would have implied too high risk for complications and open chest surgery is no option for many patients, in particular elderly patients.

Examples of the invention described below allow advantageously reducing time for part of or an entire procedure. Implantation time is shortened compared to the prior art systems, and thus for instance the total dose is advantageously reduced. The angle of the x-ray modality needs to be changed less often than required by the prior art systems. Less amount of contrast medium is needed. Over all the below disclosure provides for reducing potential side effects for the patient. Moreover, the cost of the procedure will be reduced.

The covered stents discussed herein are in an example self-expanding, or in another example expandable by another device, such as an inflatable balloon.

According to a first example, a medical device is provided. The device is a covered stent having a main body, and at least one lateral side branch connected to the main body. The lateral side branch is flexible and expandable.

According to an aspect of the disclosure, a system is provided.

The device and/or system may be used in medical procedures and methods as described herein.

Aspects of the disclosure include, but are not limited to the following.

In a first aspect, a covered stent is provided having a main body, and at least one branch, including one, two or three branches, connected to the main body. The covered stent also includes at least one bendable and/or flexible guiding element being distally permanently or releasably attached to an interior of one of the at least one the branches at a connection point, preferably at a distal orifice of the branch. The guiding element is proximally arranged in the interior, through and along a proximal portion of the main body and extends proximally through a proximal opening of the main body. In this manner a catheter can be guided over the guiding element through the main body towards the distal orifice of the branch.

In a second, a delivery catheter is provided for delivery of a second covered stent to be connected to a first covered stent. The catheter has a delivery lumen with a distal orifice for delivery and deployment of the second covered stent at a target site of a branch of the first covered stent. The catheter further has a guiding mate for receiving a guiding element distally attached to a connection point at the branch. In this manner the catheter can slide along the guiding element over the guiding mate to the orifice of the branch and the delivery and deployment of the second covered stent through the delivery lumen of the catheter. The guiding mate for receiving the guiding element has preferably a distal end positioned proximally at a distance from the distal orifice of the delivery lumen such that the delivery lumen extends beyond the connection point when the guiding mate distal end engages the connection point.

A modular system of a covered stent according to the first aspect and a delivery catheter of the second aspect with the guiding element arranged through the guiding mate for delivery of a second stent graft through the delivery catheter to the target site of the branch. The second stent graft preferably is an extension stent graft.

A modular covered stent system including a plurality of covered stents, wherein at least one of the covered stents preferably is a covered stent of the first aspect of the disclosure. The plurality of covered stents are configured to be inter-connectable to each other. The plurality of covered stents includes a first main vessel covered stent with a first single distal upstream inlet branched into at least two proximal downstream outlet branches, and at least two covered stents with at least one lateral side branch orifice. Each of the at least two covered stents is distally interconnectable to one of the downstream outlet branches of the first main vessel covered stent and laterally connectable to a side stream vessel of the main vessel. The at least two covered stents can be sequentially interconnected to one of the downstream outlets branches for providing blood conduits arranged in parallel by the at least two covered stents. The modular system includes a second main vessel covered stent with at least two distal upstream inlet branches collected in a single proximal downstream outlet, each of the distal inlet branches to be interconnected to a proximal outlet of one of the at least two covered stents.

A method for navigating a covered stent to a vascular target site, including providing a covered stent of the first aspect of the disclosure. Further the method includes delivering the covered stent to a vascular target site, and navigating a branch of the covered stent into or towards a branch vessel. The method includes providing a catheter according to the second aspect of the disclosure and arranging a guiding element attached to the covered stent through a guiding mate of the catheter, advancing the catheter along the guiding mate until an attachment point of it stops further advancing. The method includes delivering a second stent graft or a guidewire thereof through a lumen of the delivery catheter to a target site of the branch of the covered stent, the second stent graft preferably being an extension stent graft. The method optionally includes affixing the extension stent graft proximally to the branch and distally in the branch vessel.

A medical procedure including accessing a target site being a vessel in a patient and delivering a first covered stent to the inside of the vessel at the target site through a delivery catheter. The target site has a side branch vessel and the method includes delivering a second covered stent to the first covered stent and connecting the first covered stent to the second covered stent for providing a blood flow to the side branch vessel. The delivery of the second covered stent includes sliding a catheter along a guiding element to a position inside a lumen of a side branch of the first covered stent. The method may include expanding the second covered stent for connecting to the first covered stent.

A medical procedure including accessing a target site being a vessel in a patient and delivering a first covered stent to the inside of the vessel at the target site through a delivery catheter. The target site has a side branch vessel and the method includes expanding the side branch and delivering a second covered stent to the first covered stent and through the side branch to the side vessel. The method includes connecting the first covered stent to the second covered stent for providing a blood flow to the side branch vessel.

A medical procedure for aortic vessel reconstruction including delivering covered stent modules are delivered in a specific order. The method may start with implanting a three-legged covered stent in the ascending aortic arch. The method includes delivering, in downstream direction of the aorta, two parallel covered stents with one side branch each, in the aortic arch, and sequentially connecting the parallel covered stents to a leg of the three-legged covered stent and a branch vessel of the aortic arch. The method includes delivering, downstream the aorta a covered stent collecting the parallel covered stents. For instance the collecting includes providing two distal legs united into a single lumen body having a proximal orifice, connecting the two distal legs to a proximal end of one of the two parallel stents, respectively. Different number of parallel covered stents than two changes the number of legs accordingly. Intermediate collection numbers of legs may be provided by devices, systems and methods.

Further examples of the disclosure are defined in the dependent claims, wherein features for the second and subsequent aspects of the disclosure are as for the first aspect mutatis mutandis.

Some examples of the disclosure provide for an improved navigation of and assembling of a covered stent or a plurality of covered stents, each in a side branch vessel from a main vessel.

Using this innovative system, device and/or method, an operation to position a covered stent with side branch connections, in particular with multiple side vessels (up to four side branches) such with for example three or four side branches, the time needed for implantation is expected to be considerably reduced, in the range of several hours less than conventionally would have been needed. Using conventional pre-fabricated stent grafts, such a procedure takes instead much longer time, around 10 hours operation time or longer. Despite the enormous reduction of surgery time for positioning the covered stent device/system, no safety of procedure is lost. Instead safety may be improved. The delivery of the innovative device and system is very reliable. Time for implantation is significantly reduced by the novel modular system and/or its components and/or the procedure for implantation possible by the system's features. This is described in detail below.

By covered stent means a stent having a liner, shell or being otherwise surrounded by a liquid impermeable fabric or material. The covered stent can be partly or fully covered. A covered stent can also be called a stent graft or an endoprosthesis.

A side branch 3 may be laterally extendable and/or collapsible, i.e. expandable in a direction of a longitudinal axis along the side branch 3, which direction is preferably substantially perpendicular to a longitudinal axis along a main body 2 of a covered stent 1. Alternatively, or in addition, the side branch 3 may be expandable in a transverse direction, i.e. expandable transverse to the direction of an axis along the side branch 3. The side branch 3 may comprise a covered stent and may in some examples be a covered stent.

In examples, the side branch 3 is about 1 cm to 1.5 cm laterally extendable.

The side branch 3 is in an example integral with the main body 2, either by the covered stent of the main body 2 and the covered stent of the side branch 3 being integral, or by the cover of the main body 2 and the cover of the side branch 3 being integral. In an example both cover and covered stent of the main body 2 is integral with the cover and covered stent of the side branch 3. When the side branch 3 comprises the covered stent it is stiffer and can then resist more handling when e.g. deploying and/or re-deploying any further covered extension covered stent. This also allows for the side branch 3 to form a tighter connection with any further covered extension covered stent out from the side branch 3.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which

FIG. 12 is a flow chart of an example of a medical procedure;

FIG. 13 is a flow chart of an example of a method for navigating a covered stent to a branch vessel;

DESCRIPTION OF THE PREFERRED EMBODIMENTS

Figure 1:
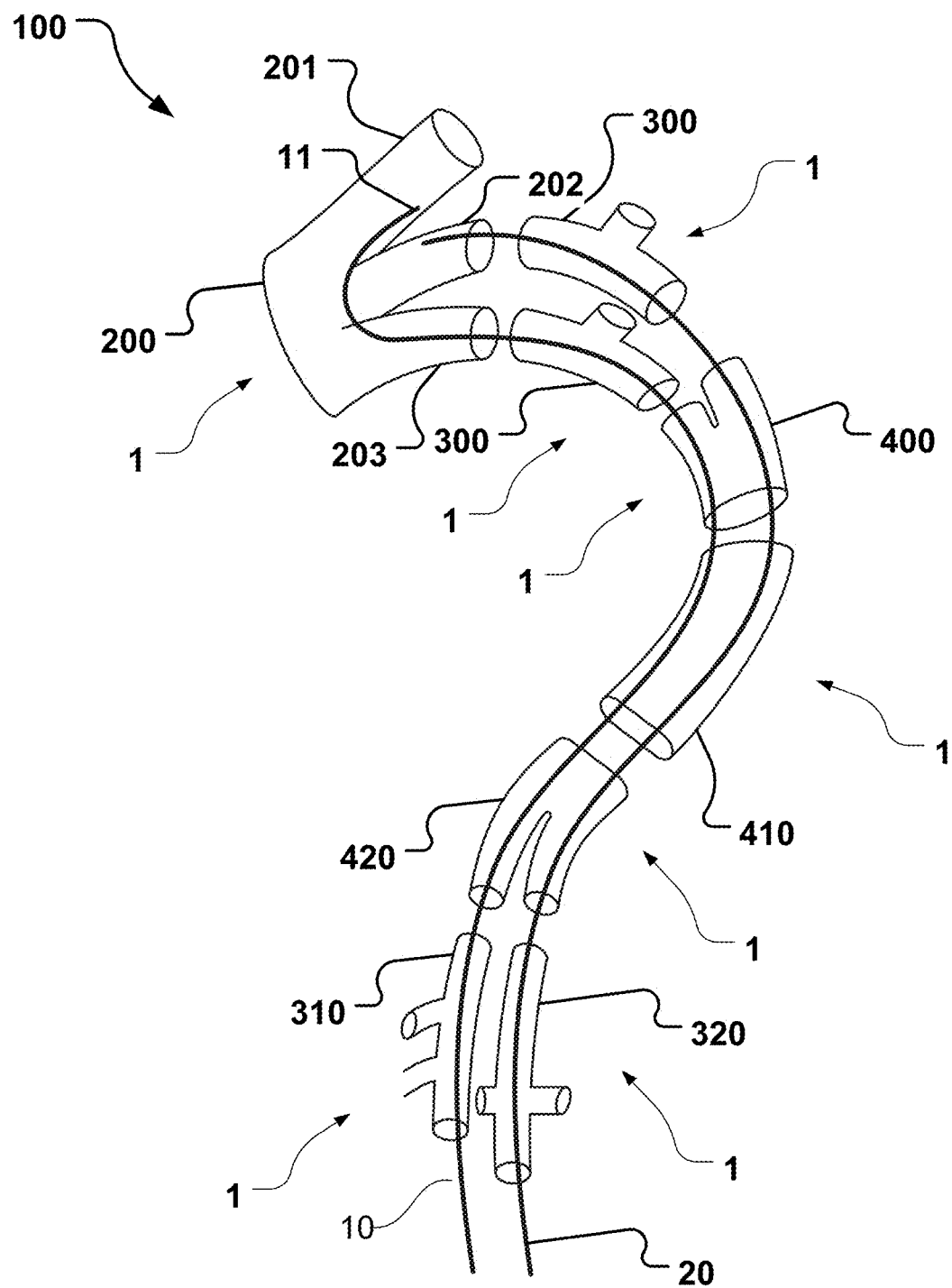
FIG. 1 is a schematic illustration that shows a system of different covered stent modules for implantation inside the aortic arch and thoracic aorta of a patient.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an example of the present disclosure applicable to a medical device and in particular to a medical device for facilitating navigation of and assembling of a covered stent or a plurality of covered stents in communication with at least a side branch vessel. The implant can be used for treatment and/or repair of vascular disease, such as e.g. aneurysm. The example is illustrated with an arrangement in the aorta. The vessel like the aorta may be structurally damaged of different reasons and need repair along at least a portion of the aorta 500. Sometimes extensive endoprosthesis are needed for aortic repair, partly or all the way from the ascending aorta 501 via the aortic arch 502 down the descending aorta 503 and along the abdominal aorta 504 past the renal arteries 505.

Figure 2:
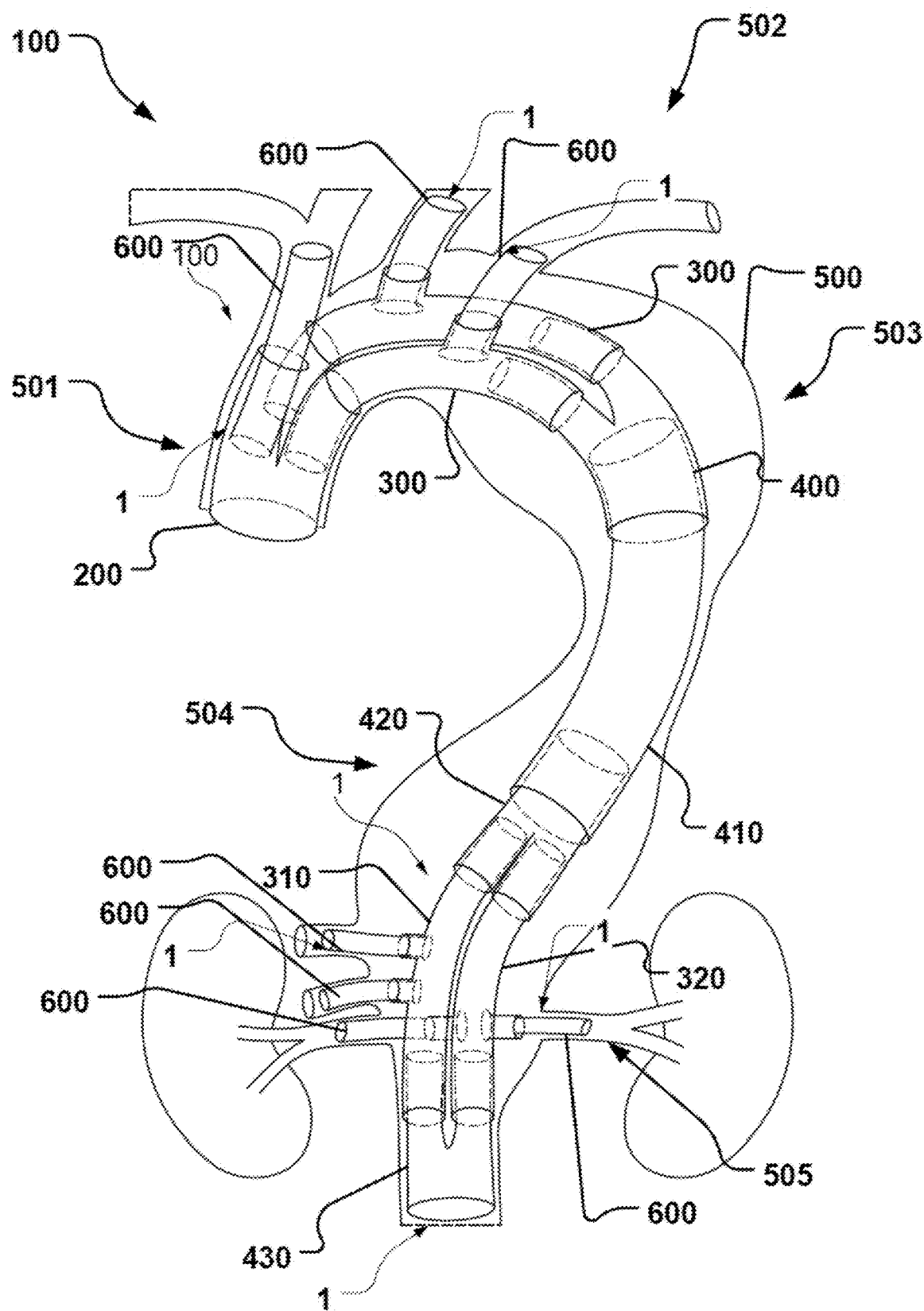
FIG. 2 is a schematic illustration that shows the system of FIG. 1 when it has been implanted inside the aorta of a patient.

An example of such an endoprosthesis including modular embodiments and assembly is illustrated in FIGS. 1 and 2 and the corresponding text herein. Total aortic reconstruction or repair can be provided when implanting the entire system as shown in FIG. 2. Partial aortic reconstruction or repair may be provided with selected sub-modules of the system being implanted only. However, other anatomical structures may be provided for treatment with the devices and/or systems of the disclosure, including abdominal covered stents, peripheral stent grafts, endoluminal prosthesis, and include e.g. but not limited to peripheral veins, leg arteries, spinal vessels, neuro structures, lymphatic system, etc.

FIGS. 1 and 2 show a system of various covered stent modules 200, 300, 310, 320, 400, 410, 420, 430, 600 for implantation inside the aortic arch 502 and abdominal aorta 504 of a patient. FIG. 2 shows the system 100 of FIG. 1 when it has been implanted inside the aorta 500 of a patient and the modules being connected to each other. Further extension stent grafts 600 not shown in FIG. 1 are connected and shown in FIG. 2. A reliable communication of blood is provided through the prosthesis in a main vessel, here the aorta 500, and into branch vessels, here to neck vessels, renal arteries 505 and others. The aortic wall is in the example illustrated with weakenings/aneurysms in the descending aortic arch and abdominal aorta, needing treatment provided by the exemplary stent graft system 100 for aortic replacement/repair.

In the illustrated example, a number of covered stents 1 (reference sign "1" cited together in this specification can be regarded a placeholder for "covered stent" or "covered stents", e.g. of the types disclosed herein, as for instance covered stents 200, 300, 310, 320, 400, 410, 420, 430, 600 etc.) is assembled and interconnected to fit inside parts of, or the entire, aorta of a patient to form a system 100 or a modular sub-system thereof. The covered stents 1 discussed herein may also be implantable in other target sites of the body for repairing and/or re-building conduits of vessels for liquid communication through the vessels.

FIG. 1 illustrates different kinds of modular covered stents 1 that can be used for an exemplary assembly of the system 100 of modular covered stents 1 that fit inside the vessels of and around the aortic arch 502 of a patient. The system 100 may be assembled in vivo or in vitro.

Alternatively, systems may include more or fewer covered stent modules. For instance, only the aortic arch may be covered by modules like covered stents 200, 300, 310, 320, 400, 410—all depending on the treatment site and treatment needs. Other examples of combination of covered stent modules are: a) 200, 2×300+2×600, 400 and optionally 600 in 201; b) 420, 310+optionally 2×600, 320+optionally 2×600, and 430; c) intermediate 410+example a) and b); etc.

Some of the covered stents 1 have side branches 3 that are provided to extend blood communication through the system, and preferably into branch vessels. Examples of such covered stents are modular covered stents 300, 310, 320.

Some of the covered stents 1 have legs, i.e. the main body 2 of the covered stent 1 branches into two or more tubular parts. Examples of such covered stents are modular covered stents 200, 400, 420, 430.

Alternatively, or in addition, and although not shown in the figures, a covered stent 1 may have both side branches 3 and legs. Covered stent 200 might be considered an example having two legs 202, 203 and a side branch 201. Both legs and side branches can be considered being branches in the present context. Other covered stents, not discussed or shown herein but commonly used today may also be used in the system 100.

The modular covered stent system 100 comprises a plurality of covered stents 1, wherein at least one of the covered stents is a covered stent 1. The plurality of covered stents 1 are configured to be interconnectable to each other.

Alternatively, or in addition, the system further comprises an elongated navigation element 20, which allows the operator to navigate the covered stent and/or the side branch 3 of the covered stent 1 and align the side branch 3 with branch vessels. The elongated navigation element 20 is preferably a guide wire, such as shown in FIG. 1.

In an example, the covered stents have a substantially identical diameter at an inter-connection between two covered stents to provide a liquid tight interconnection.

In an example, having the same diameter at an inter-connection means that the outer diameter at the inter-connection of one of the covered stents is substantially the same as the inner diameter at the inter-connection of the other covered stent, at least along a portion of the covered stent. The same diameter is maintained at least along an overlapping portion of the two covered stents, if overlapping. The two covered stents are thus for instance liquid conveying connectable by overlapping each other and one tube inside the other connected tube.

The stent structure of covered stents is part of the covered stent. It may have a pattern, like undulations. The pattern may be made by made by braiding, weaving, laser cutting of a tube, etc. The structure is a scaffold to support the structure outwards and provide a substantially tubular structure to ensure undisturbed blood flow through the tube when implanted as it is provided with and covered by a suitable liquid tight cover.

The undulations or pattern can be denser at the overlapping connection region than other regions of the covered stent—for a secure liquid tight connection of two covered stents and by improved mechanical strength.

Figure 19A:
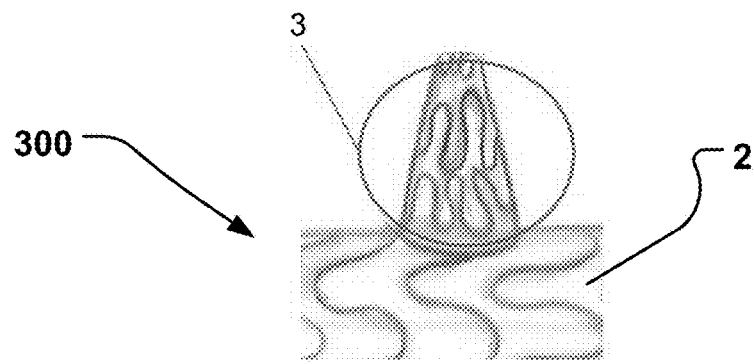
FIGS. 19A, B and 20 are schematic illustrations of different stent patterns of a lateral side branch.

FIGS. 19A, B and 20 are schematic illustrations of some exemplary stent patterns/undulations of a lateral side branch.

Figure 19B:
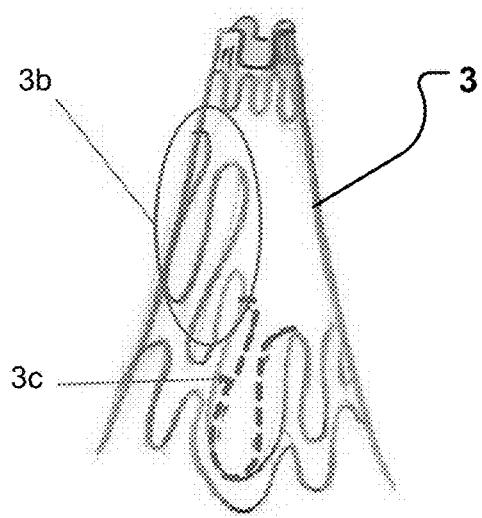

The pattern in FIG. 19A shows a wavy (nitinol) wire or laser cut structure that is easy to reduce its outer diameter and to fold it down beside the prosthesis main body into a delivery configuration. Upon release from a catheter or removal of a restraining member, it will resiliently expand longitudinally, as will the designs of FIG. 19B and FIG. 20.

The pattern in FIG. 19AB has a region without a supporting frame in the zone 3b that the extension prosthesis 600 will overlap with. The frame pattern has an asymmetrical design. The dotted line 3c in the Figure indicates an area that will encourage the stent to collapse. This design requires less force to fold and less space to store it for delivery in an outer sheath. The portion with a longer support frame (in the left of the Figure will ensure the side branch prosthesis is expanded in a sufficient length which will stay in the side branch or be oriented radially outwards from the main body.

Figure 20:
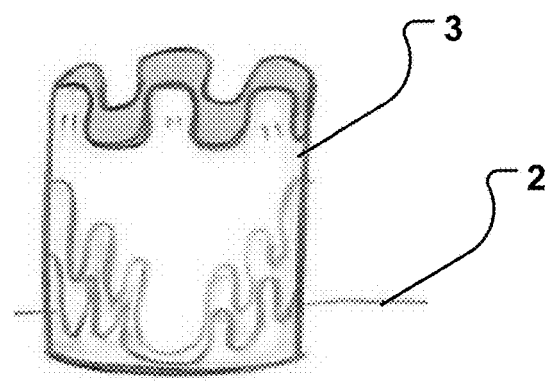

The pattern in FIG. 20 shows two halves of a frame pattern that will advantageously collapse to the middle. Also this design requires less force to fold and requires less space to store it for delivery in an outer sheath.

The collapse of side branch 3 for delivery through a catheter may be obtained in multiple ways. It may be folded back, slid sideways along the catheter inner lumen, or compressed along its longitudinal axis. If a cover is provided (FIG. 9 etc.) the side branch, and covered stent, are collapsed and held inside the cover/restraining member 8. The restraining member 8 may be of a material with low friction, such as PTFE. The restraining member 8 allows for a pull/push release of a covered stent contained in the restraining member 8 during delivery until deployment. Alternatively, or in addition, the inside of the catheter may be provided with a good sliding property material to facilitate movement of the covered stent along the inner lumen to the target site, with the restraining member optionally covering the covered stent during delivery until final deployment.

In another example having the same diameter means that the two covered stents to be connected have substantially the same inner diameter at the inter-connection and are connected in a non-overlapping manner, e.g. end to end connected. An additional inner liner may be provided at the connection site of the two covered stents, preferably downstream entering the inner of the downstream oriented covered stent from the upstream positioned covered stent.

In an example the two covered stents to be interconnected have both substantially the same inner diameter and substantially the same outer diameter at the interconnection, and the covered stents are connected by overlapping them when one of the covered stents is in a partially collapsed or folded state.

Having covered stents with the same or substantially the same diameter makes it easy for the operator to connect the various covered stents since the diameter of corresponding covered stent parts of the system 100 is similar and the operator does then not need to worry about any particular connection method, stent shape, connection site or the like. This means that the operator does only need to consider if the previous covered stent were a single, double, triple or further legged covered stent. This also makes the production of the covered stents easier since the diameter at the connection of the various covered stents are the same. An example is the diameter of legs 202, 203, covered stent 300 main body, and upstream oriented legs of the covered stent 400.

The overlapping region allows for length adaptation of the modular system. For instance the modular covered stents, 400, 410, 420 could be provided as a single integral unit. However, providing straight middle piece covered stent 410 separate from branched end piece covered stents 400, 420, allows for adjustment to specific patient anatomy (in the example different length of abdominal aorta). Overlap of the middle covered stent can be varied accordingly. Length adjustment of a system of modular covered stents is provided by an overlapping portion at openings of covered stents allowing for varying overlap and determining total length of the assembled modular system upon implantation. This applies, mutatis mutandis to side vessel extension covered stents 600 connections, etc.

In the prior art, systems of covered stent modules are provided with covered stents that have a varying diameter in e.g. a tapered shape. They are connected by inserting a first folded tapered shaped covered stent into a second expanded tapered shaped covered stent. When the first covered stent is expanded, the two covered stents form a connection. Such a system causes an unnecessary additional task for the operator to keep track of in addition to keeping track of all the covered stent modules not only being in the right order, in the right direction before and during the entire operation but also need to keep track of where and how these two cones fit to each other. In contrary, examples of the present disclosure provide for a simpler, safer and quicker procedure of implantation.

Providing the covered stents 1 with substantially the same diameter gives the advantage that the operator can implant each covered stent 1 as explained above, or in an example in any direction he or she thinks is best. This will shorten the time required for assembling the system 100 and consequently the operation, drastically.

In an example, when the covered stent 1 has substantially the same diameter as discussed above and is expanded, or when a side branch 3 or leg of the covered stent 1 is expanded, a flow through the covered stent 1 is more or less unchanged through it. Meaning that a liquid, such as blood, entering at one side e.g. the main body 2 will pass through the covered stent 1 and out through e.g. two legs at the other side and due to the expansion and same diameter of connection at the covered stents 1 an inlet and outlet area are substantially the same. This allows the operator to concentrate on connecting one covered stent 1 or part of a covered stent 1, such as a leg, at the time. The operator needs not to worry about the covered stent 1 disturbing the flow or throughput in the covered stent 1 or vessel.

Additionally, this allows for using a covered stent or a plurality of covered stents in a system and assembly at the implantation target site, i.e. not pre-manufactured for a specific patient. This is an advantage over known systems. Known systems included hitherto pre-built, patient specific endoprosthesis. Usually, an image modality is used to scan the vessel system including the target site, e.g. a weakened aorta, earlier in time. The endoprosthesis is then manufactured based on the imaging data and delivered to the surgeon for implantation. This manufacturing of a patient specific endoprosthesis usually takes days to weeks, which is undesired. The anatomy of the vessel may change during this waiting time. The consequence may be that the manufactured endoprosthesis does not fit the patient anymore. Also, the waiting time is undesired as the patient mostly is in immediate need of the endoprosthesis, e.g. to avoid rupture of an aortic aneurysm. If desired, however, specific embodiments of the covered stents of the present disclosure may be manufactured patient specifically. A standard setup of different sizes readily available for implantation is preferred, though, as waiting time due to manufacturing is avoided.

The modular covered stent system 100 may further comprise a guiding element 10, like a suture or wire. Along guiding element 10 a delivery catheter may be threaded proximally to the distal end of the guiding element 10. The guiding element 10 is distally affixed to a covered stent, for instance a suture may be affixed by means of a knot, staple, weld, adhesive, or similar. The guiding element 10 is thus secured to the covered stent. Preferably, the attachment point where the guiding element 10 is distally secured to the covered stent is at the interior, e.g. at a location of a lateral side branch of the covered stent. The guiding element 10 is preferably pre-loaded in a delivery catheter of the covered stent. The guiding element is in use operating as a guilder for a guiding mate 9 of a catheter. The guiding element 10 is preferably bendable and/or flexible. bendable and/or flexible.

In embodiments, the guiding element 10 is thus distally permanently or releasably attached to an interior of a branch, e.g. a lateral side branch, at a connection point, preferably at a distal orifice of the branch 3. The guiding element 10 is proximally arranged in the interior, through and along a proximal portion of the main body 2 or another of the branches 3 and extending proximally through a proximal opening of the main body 2 (see e.g. FIG. 3 or 8). In use the guiding element is thus operating for guiding a catheter over the guiding element 10 through the main body 3 towards the distal orifice of the lateral side branch 3.

See FIG. 3 or 8 and the corresponding text below for more detailed described examples of the guiding element 10 and its corresponding use and application in a modular stent graft system.

Alternatively, or in addition, a guiding element 10 can be distally attached to the aorta of a patient at a desired target location.

Alternatively, or in addition, the attachment of a guiding element at its distal end may be releasable, preferably releasable from outside the body activation, for removing the guiding element during the implantation procedure, as needed. A knot may be releasable, thermal detachment means may be provided for controlled detachment of the guiding element at the attachment point. Alternatively, or in addition, the guide element may be configured to be cut off after use. Suitable tools may be used for the cutting off, e.g. a sheath with an interior secure cutter slid over and along the guiding element towards the attachment point, where the cutter is activated and the guiding element cut off. The guiding element may then be securely retracted out of the body, e.g. within the sheath having the cutter, or just proximally drawn out of the vasculature via the puncture site/introducer.

However, the guiding element 10 is preferably left in place upon concluded implantation procedure. The guiding element 10 can be left in place after use (guiding delivery and deployment of e.g. an extension stent graft). It may be made of a biodegradable material or bioabsorbable material. The guiding element 10 is in any case made of a biocompatible material, including absorbables such as polyglycolic acid, polylactic acid, Monocryl and polydioxanone as well as the non-absorbables nylon, polyester, PVDF and polypropylene, PTFE or Dacron. The guiding element 10 may be made of metallic material, such as Nitinol or stainless steel, or a suitable metal alloy, which might be advantageous from a durability advantage during implantation. This is advantageous when the guiding element is left in place after concluded implantation procedure of the modular covered stent system. The procedure can be shortened as the guiding element needs not to be detached or cut off at or close to the connection point. It may be cut of at is proximal end only, or not at all.

Figure 8:
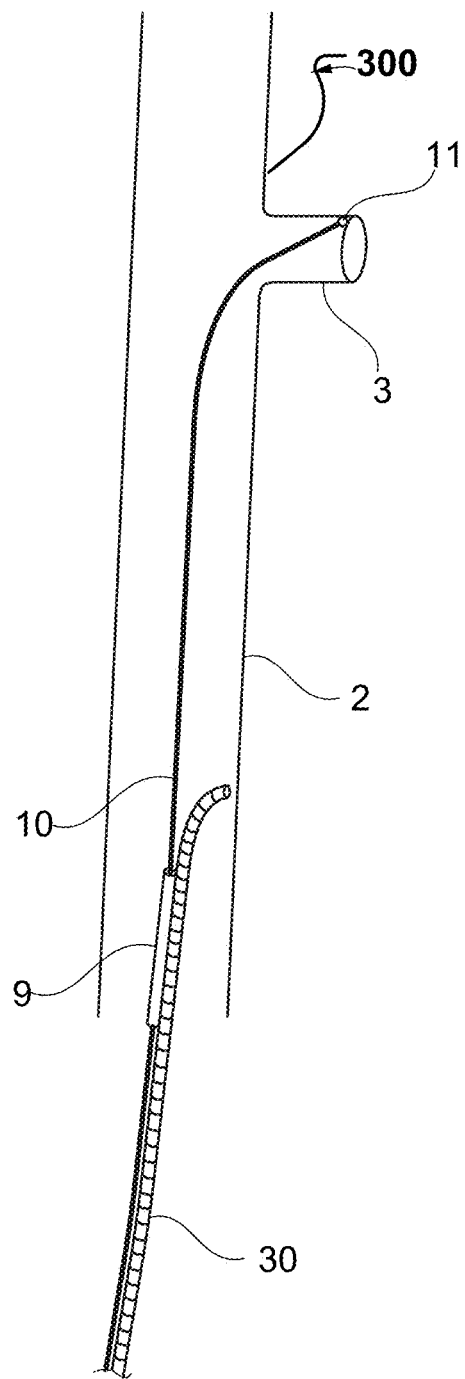
FIG. 8 is a schematic illustration of a covered stent with a side branch, and a catheter with a guiding mate for guiding the catheter for easy navigation of the side branch.

Along guiding element 10, the delivery catheter 30 may be moved towards the distal end of the guiding element 10, e.g. by means of a guiding mate 9 on the catheter as described below (FIG. 8). Delivery of another element, device or unit, can then take place through this delivery catheter to a desired site at the distal end of the guiding element 10. X-Ray guidance, probing, navigation tries etc. can advantageously be reduced or omitted.

In this manner, a catheter can be moved along the guiding element to or towards the distal end thereof without fluoroscopic guidance. In this manner, reliably, and speed of delivery is improved while radiation exposure can be reduced.

Such a delivery catheter 30 is provided for delivery of an extension stent graft 600. The catheter 30 has a delivery lumen with a distal orifice for delivery and deployment of the extension stent graft 600 at a target site of a lateral side branch 3 of a covered stent 1.

The catheter 30 further has a guiding mate 9 for receiving a guiding element 10 distally attached to a connection point at the branch 3. Therefore, the catheter 30 is configured to slide along the guiding element 10 over the guiding mate 9 to the orifice of the branch for deployment of the element, such as the extension stent graft 600 through the delivery lumen of the catheter.

The guiding mate 9 for receiving the guiding element has a distal end positioned proximally at a distance from the distal orifice of the delivery lumen. In this manner the delivery lumen extends beyond the connection point when the guiding mate 9 distal end engages the connection point.

As can be seen e.g. in FIG. 8, the distal end of the delivery catheter 30 may be pre-bent to advantageously enter into the side vessel from the branch orifice. In this manner the operation time is reduced, fluoroscopic load of the patient and clinical personnel reduced, and the implantation made more securely and reliable.

A modular stent graft system is provided including a covered stent 1 and a delivery catheter 30 with a guiding element 10 arrangeable or arranged through a guiding mate 9. In this manner a unit, such as an extension stent graft 600 is advantageously deliverable through the delivery catheter 30 to a target site at a branch 3.

In addition, the distal end of the guiding element 10 is for example arranged at a marker 21. Alternatively, or in addition, the guiding element 10 may be provided itself with a marker. Marker means fiducial marker that is visualizable by suitable imaging means for the surgeon performing the implantation procedure. The marker 21 is preferably arranged at a leg 4 of a covered stent for guiding delivery of another covered stent towards and/or through the distal orifice of such a leg 4, e.g. as described below, to a side branch vessel of a main vessel. The marker may be elongate and extend along at least a part of the length of the guiding element 10, e.g. as a radiopaque strand of a multi-strand wire/suture/thread, and/or one or more marker bands.

To make it easier to position another covered stent in relation to a leg of a first covered stent the marker 21 is provided at e.g. the leg of the first covered stent. In the same way a marker 21 may be provided on the side branch 3 of a covered stent 1, allowing easier aligning of the covered stent 1 in relation to a branch vessel. X-Ray may then be used for position confirmation, which means a reduction of dosage compared to full X-Ray supported navigation with contrast medium.

The illustrated modular covered stent system 100 includes a first main vessel covered stent 200, 420 with a first upstream inlet branched into at least two downstream outlet branches.

Further it includes a covered stent type 300, 310, 320 that has a main body, and at least one lateral side branch connected to the main body. The lateral side branch is preferably flexible and expandable. The covered stent is interconnectable to one of the downstream outlet branches and laterally connectable to a side stream vessel of the main vessel via the lateral side branch thereof. At least two covered stents 300, 310, 320 are thus sequentially interconnectable to one of the downstream outlets of the main vessel covered stent 200. In this manner, blood conduits are provided arranged in parallel by the at least two covered stents, one at a time assembled by the operator. The parallel blood conduits may be provided with one or more side branches each. Alternatively, or in addition, a blood conduit in form of a covered stent may be provided that has no lateral side branch, which then provides a straight blood flow path in parallel with e.g. a covered stent having one or more lateral side branches.

The parallel arrangement of covered stents has several advantages. Repositioning of one of several parallel covered stents is more easily performed than that of a single covered stent covering the entire vessel with multiple side branches. It is easier to sequentially implant several parallel covered stents with one or few branches than one large covered stent with many branches. The proximal and distal ends of the covered stent 300, 310, 320 are not stented into vessel tissue wall. Mechanical stability and attachment are thus better controllable than in relation to an anatomical structure, in particular if this is weakened such as at an aneurysm. As the parallel covered stents 300, 310, 320 can accommodate movements of the vessels better, this is an advantage. There is less risk of damaging the tissue vessel as contact is reduced, which positively affects long term implantation stability of the modular system. Adaptation to anatomy at implantation is made easily by the surgeon as rotation and longitudinal position are adjustable intra operatively. No aortic clamping is needed and cardioplegia is avoided, which reduced side effects for the patient and makes the procedure quicker, and reduced patient risk. As each of the parallel covered stents 300, 301, 320 has a lesser diameter than the vessel into which they are implanted, a distance to side branches from the covered stent main lumen is provideable. This in turn allows for navigational space of the covered stent in relation to a side branch vessel orifice. Positioning of the side branch of the covered stent in relation to the orifice is thus less critical than for known systems. Compensation can be made thanks to the distance between the side branch of the covered stent and the orifice of the side vessel's orifice, e.g. by bending a side branch and/or by bending an extension covered stent 600 without kinking one or both of the latter mentioned when implanted from the main vessel into the side vessel.

The modular covered stent system further includes a second type of main vessel covered stent 400, 430 with at least two upstream inlet branches collected in a downstream outlet. The inlet branches are interconnectable to a distal outlet of one of the two covered stents, e.g. covered stents type 300, 310, 320 as shown in FIGS. 1 and 2.

Starting from the top of the system 100 as illustrated in FIGS. 1-2, there is illustrated a first covered stent 200 with three legs. This module is implanted firstly over a guidewire 20.

It should be noted that the covered stent modules are delivered in a specific order, starting with a three-legged covered stent 200 in the ascending aortic arch. Further covered stent modules are then delivered to the target site until the entire system is implanted. This is done in a very efficient and advantageous manner.

For instance, when the three legged covered stent 200 is deployed and implanted firstly of all modules in the ascending aortic arch. This can be done via a guide wire 20, e.g. in a femoral access approach. Further components can then be connected to the legs 201, 202, and/or 203.

For instance a covered stent 600 can be delivered to the first leg 201 via a delivery catheter slid along guiding element 10 to or towards connection point 11, such as in the manner described with reference to FIG. 8. This covered stent 600 can then extend blood flow into the first neck side vessel as shown in FIG. 2. The covered stent 600 is a covered stent without apertures for side vessels. The extension stent graft 600 is configured to be proximally matingly and fluid tight connected to the distal portion at the orifice of the first leg 201. Connection may be done overlappingly in a suitable manner and by suitable means known in the art of connecting stent grafts to each other for providing a communication channel for liquid there through to the target vessel.

Delivery is thus provideable in two steps. Firstly, the side branch 3 is expanded. Then a side vessel covered stent 600 is deployed through the expanded side branch 3. Fixation of the side vessel covered stent 600 is done then. The entire prosthesis is flexible until the side branch is finally intubated, i.e. the side branch covered stent 60 is deployed and thus "locked" in position.

During delivery of covered stent 600, the two remaining legs 202, 203 are not obstructed and blood flow through the aortic arch is ensured during the implantation procedure, which is an important advantage.

The guiding element 10 is also running inside the third leg 203. This means, that over same guiding element 10 and delivery catheter over which the covered stent 600 was delivered, the covered stent 300 with a side branch is deliverable.

The initial guidewire 20 for delivering the three-legged covered stent 200 to its target site, is used for delivering and connecting a covered stent 300 to the second leg 202.

The location of three-legged covered stent 200 is preferably marked with a fiducial marker 21 that can be seen during imaging by e.g. MRI, CT or X-ray. Hence, shortened radiation times and dosages are provideable.

As the guiding element 10 extends out from the first leg 201, all three legs can be located and modular covered stents interconnected at the orifices of the three legs. No additional navigation, searching or probing by the surgeon is needed, thus reducing radiation times and dosages.

The guiding elements 10 are for guiding subsequent covered stents along them so that the subsequent covered stents can be connected to a previously implanted covered stent.

In addition, or alternatively a navigation element 20, such as a guide wire, is used instead for or together with one or more guiding element(s) 10 in the system 100 for guiding all or almost all of the covered stents of the system 100 to their target site.

Next, the system 100 includes in proximal direction, downstream the aorta, two covered stents 300 with one side branch each, positioned in the aortic arch 502 upon implantation. The two covered stents 300 are each guided by the guiding elements 10 and guidewire 20, respectively. These modular covered stents 300 are described in more detail below, e.g. with reference to FIGS. 5a, 6, 7, 8, 10, 11, 14, 15, 17, 19 and 20. Each of covered stents 300 is distally connected to a leg 202, 203 of the three legged covered stent 200. The side branch exit is preferably expandable, and in liquid communication with a neck vessel when expanded. A further covered stent 600 is further connected with its proximal end, respectively, extending into the remaining two neck vessels respectively (see FIG. 2). Delivery of these further covered stents 600 can be done fiducial marker guided (not shown), with guidewires and contrast medium feedback, and/or a guiding element 10 can be connected to the branch (see FIG. 8) facilitating delivery of the further covered stents 600 through the orifice of the side branch of covered stent 300 and into the respectively neck vessel.

Delivery of each covered stent 300 and extension is done sequentially. While delivering the first of these two units 300, the other leg of three-legged stent 200 is not obstructed and blood flow through the aorta ensured. Also, when delivering the extension into a neck vessel, blood flow both downstream the aorta and into the neck vessel is uninterrupted during the procedure.

When both covered stents 300 are interconnected and delivered, a parallel flow through the aorta is provided with sufficient blood flow needed due to a high ratio of lumen diameter to (healthy) aorta diameter.

As the orifices of the lateral branches can be located at a distance from the ostia of a target site vessel thanks to the parallel arrangement of several covered stents 300, the exact position in relation to each other (ostia/orifice) is not as important as for known covered stents. Flexibility without risk for kinking is provided with or without extension covered stents 600.

Then, downstream the aorta there is proximally a covered stent 400 with two distal legs united into a single lumen body having a proximal orifice. The first leg of covered stent 400 is delivered running along guiding element 10 for interconnection with the proximal orifice of the covered stent 300, which in turn is previously distally interconnected to the third leg 203 of the distally and upstream in the aorta arranged and previously implanted covered stents 300. The other distal leg of covered stent 400 is delivered along guidewire 20. It is distally interconnected to the proximal orifice of the other covered stent 300, which in turn is previously distally interconnected to the second leg 202 of the distally and upstream in the aorta. Thus the parallel covered stents 300 are collected together in a single lumen.

A further covered stent 410, without side branches or legs is distally interconnected to the proximal orifice of covered stent 400. The further covered stent 410 is delivered over both the guiding element 10 and guidewire 20 which both are run inside this covered stent 410 through one of the distal legs of covered stent 400 respectively. In case the covered stents 300 include one or more guiding element(s) 10, previously used for the extension covered stents into the neck vessels, these one or more guiding element(s) 10 will also be run through the lumen of covered stent 410.

Overlap of covered stents 400, 410, 420 can be adapted during implantation to accommodate the patient aortic anatomy.

Next in downstream aorta direction is a two-legged covered stent 420 is implanted/provided and branching the blood flow into two proximal legs from a distal common lumen and orifice interconnectable to proximal orifice of the distal covered stent 410 previously implanted. Guiding element 10 runs inside the first leg. Guidewire 20 runs inside the other leg. The two legged stent is delivered over the two latter in a delivery catheter, which may be the same as used for delivery of previously distally delivered modules.

And finally, at the bottom of the drawing, two covered stents 310, 320 are illustrated, with two side branches 3 each. These two covered stents 310, 320 are described in more detail below with reference to FIGS. 5a and 5b respectively.

The first covered stent 310 is delivered by means of guide element 10 (catheter slid over guide element 8 to the leg of covered stent 420). A further delivery catheter may be used for this purpose, such as described with reference to FIG. 8 with the difference that the guide element runs all the way through the first covered stent 310. One or more further guide element(s) 10 may be attached to one or more of the side branches of the first covered stent 310 for delivery of extension covered stents 600 extending into side vessels, see FIG. 2 when implanted.

The second covered stent 320 is delivered by means of guidewire 20. A delivery catheter is again used for this purpose, such as described above. A further guide element may be attached to one or more of the side branches of the second covered stent 320 for delivery of extension covered stents 600 extending into side vessels, see FIG. 2 when implanted.

The proximal end of the two covered stents 310, 320 are interconnected to two distal legs of a two legged covered stent 430 to provide a liquid path thereby. Guidewire 20 and guide elements 10 run accordingly through covered stent 430.

As described above, the system 100 is thus positioned as shown in FIG. 2.

In an example a method of interconnecting a plurality of covered stents is provided which can be performed either in vivo and/or in vitro.

In an example, before assembly, and/or during assembly, the covered stents of the system 100 are sorted and placed in the correct order for assembly. In an example, and if assembled during implantation, a number of catheters 30 may be used as described and needed. The components of the system may be provided as a kit with suitable numbering to facilitate implantation for the surgeon. The kit components and composition may be computer plant prior to the implantation procedure. A software may be provided to support the surgeon and/or clinical personnel to perform the procedure. The surgeon may virtually plan the procedure in advance. Sequence of components, preferably with numbers in the kit components, and procedural steps may then be suggested by software during the implantation procedure. Quality assurance may be provided by entering into the software feedback of components used and steps performed. X-ray images and timestamps and other medical equipment measurement or input data may be saved too. The procedure may thus be efficiently performed and documented at the same time.

Although not shown in FIG. 1, further navigation elements 20 and/or guiding elements 10 may be provided for navigation of the side branches 3 and aligning of the side branches 3 with branch vessels, as explained. To make it easier to see which navigation element 20 or guide element 10 that goes to a certain covered stent, leg or side branch, each navigation element and guide element is labelled in an example.

Modular covered stents, as described with the system 100 will now be described in more detail. As mentioned above, the modular stents maybe arranged differently in other systems than the one illustrated in the figures. Some modular covered stents may be provided individually for connection to known units, or individually, depending on the target site, treatment need and/or patient history.

Figure 3:
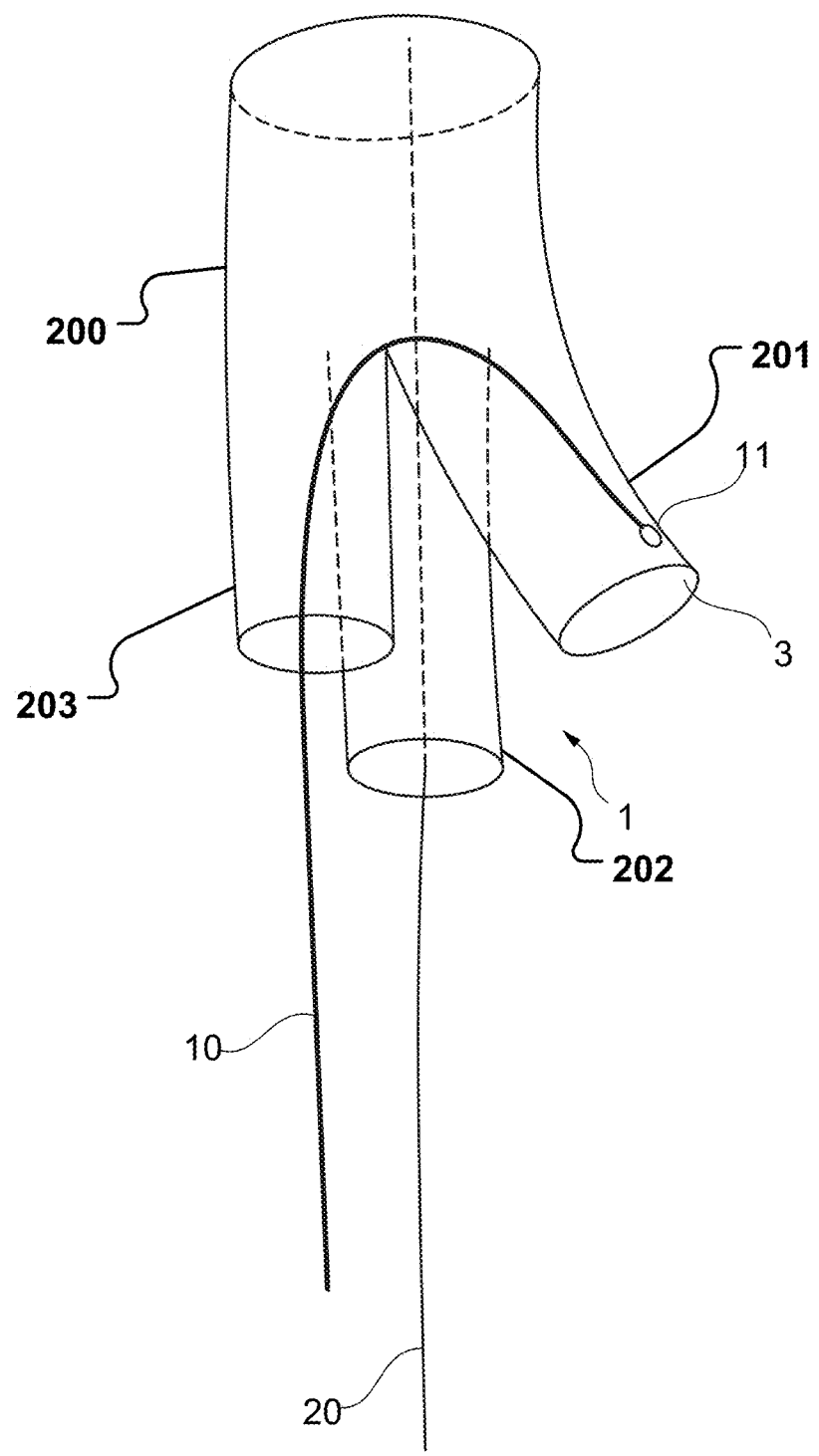
FIG. 3 is a schematic illustration of a covered stent with three legs, and a navigation element and a suture for easy navigation to all three legs.

FIG. 3 illustrates a covered stent 200 with three legs 201, 202, 203, and a navigation element 20 and guiding element 10 in from of a suture for easy navigation to all three legs. FIGS. 3 and 8 illustrate examples of how one or more (one shown) guiding element 10, such as a suture, may run through a covered stent during implantation of a system 100 of covered stents.

The three legs 201, 202, 203 are provided for connection to three aortic arch side vessels: one into the neck artery, and two through channels (when assembled) with side branch vessel connection. The three legs 201, 202, 203 may have different lumen diameter and length. Overlap with covered stents 300, 600 may be chosen according to patient anatomy during the implantation procedure.

The pre-attached guiding element 10 extending into one leg (203) and into another leg (201) allows for a direct intubation of a side vessel. Direct access is provided to all side branches of the prosthesis without the difficulty of locating the side branches with the open legs of such an implant. This has hitherto been difficult to navigate, due to the length of the delivery catheter where the operator usually has no feeling for targeting to a side vessel. Also the pulsating blood flow during the procedure, and other procedural difficulties of intubation of side branches, are less relevant than for known covered stent. 3D to 2D visualization difficulties are avoided, less x-ray dosage is needed, the procedure is provided with significant time reduction, and reduced patient risk.

The guiding element 10 is used for guiding further covered stents to a connection location so that the covered stents can be connected together into to the system 100 of covered stents. More about FIG. 8 can be found below.

In an example as illustrated in FIG. 3, the navigation element 20, here a guide wire, runs inside and through the three legged covered stent 200 via a leg 202. During implantation of the system 100, the navigation element 20 is inserted far enough into the vessel so that any covered stent can follow the navigation element 20 to a desired target site location.

In an example, the covered stents are guided to their respective position by sliding them along a navigation element 20 inside a delivery catheter. Upon release out of the distal catheter end, the covered stents are expanded into place and implanted at that target site. Restraining members 8 may be provided.

FIG. 3 further illustrates that one or more guide elements 10, such as sutures, may be attached to the covered stent 200. In the figure, the suture 10 is attached inside the second leg 4 and extends out through the third leg. The guiding elements 10 have, as discussed above, a similar purpose to the purpose of the navigation element 20 of guiding delivery catheters for delivery of covered stents such that they can be connected to form the system of covered stents 100.

The operator can easily locate the two legs and navigate further covered stents to any of the two legs. The operator can via the guiding element 10 navigate a first further covered stent 600 to the leg 201 where the guiding element 10 is attached. When the first further covered stent 600 is correctly positioned and connected to the three-legged covered stent 200, the operator can, via the same guiding element 10, navigate a second further covered stent to the leg 203 where the suture exits proximally from the three legged covered stent 200. The navigation element 20 ensures that the operator can locate also the third leg, as shown in FIG. 3, and deliver units that way as desired.

Generally, one advantage of using the guiding element 10, such a suture, instead of or in addition to the navigation element 20, such as a guidewire, is that a suture or a wire is provided flexible and can be bent and manipulated as desired without breaking. The navigation element 20 when being a guidewire is usually stiffer such that it can exert a distal force from the operator for e.g. pushing along a vessel from a puncture site. A catheter is then thread over the guide wire and moved along the guide wire. The guide wire may then be removed from the catheter for delivery of a unit through the catheter.

The flexible characteristics of the guiding element 10 allows for e.g. the covered stent to be placed into positions and/or navigated around e.g. corners in the covered stent and/or in a vessel and/or side branch 3. The guiding element 10 runs in embodiments outside of a delivery catheter lumen through which a unit is deliverable. Alternatively, or in addition, a guiding element may run through the same lumen as the lumen for delivery of a unit.

Figure 21:
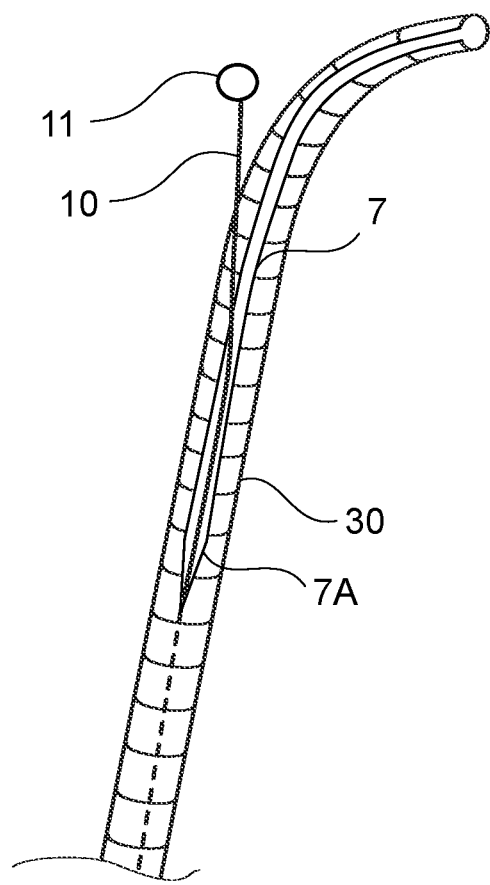
FIG. 21 is a schematic illustration of a longitudinal recess with a V-shaped access in the catheter lumen wall for catching the guiding element.

Preferably the distal tip of the catheter 30 then has a design such that the distal orifice extends beyond the attachment point of the distal end of the guiding element 10. This can for instance be provided by a longitudinal recess 7 (shown in FIG. 21) in the catheter lumen wall into which the guiding element 10 fits. The distal end of the catheter 30 with its delivery orifice may then protrude beyond the attachment point 11 where the proximal end of the recess 7 will be positioned when the delivery catheter 30 is pushed distally forward. The recess 7 may be a longitudinal slit. The recess may have at least a V-shaped portion 7A to allow the guiding element 10 to be caught or introduced more easily in the recess 7. The catheter 30 may be slightly wiggled and/or rotated to allow the guiding element 10 to enter the recess 7.

As explained previously in relation to guiding element 10, the position 11 where the distal end of the guiding element 10 is permanently or releasably attached to the covered stent is advantageously provided with a marker, so that it can easily be seen during scanning by e.g. MRI, CT or X-ray. The connection point 11 serves as a stop unit for guiding element 10 to prevent a tangible resistance and further distal advancement of catheter 30 by the surgeon during the delivery procedure.

Figure 4:
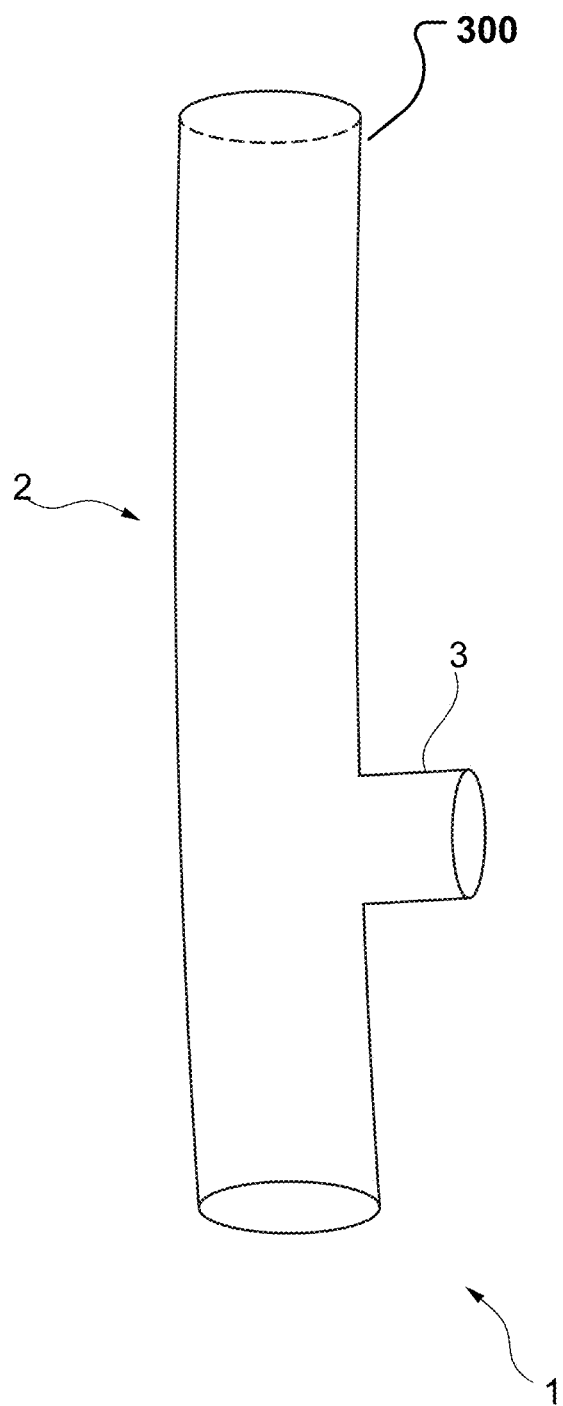
FIG. 4 is a schematic illustration of a covered stent with a side branch.

FIG. 4 illustrates a covered stent 1 with a side branch and is an example a covered stent 300 with a side branch 3 of the exemplary system 100 (FIGS. 1 and 2).

The covered stent 1 has a main body 2, which is a covered stent, and a lateral side branch 3 connected to the main body 2. The side branch 3 protrudes out from the main body 2 and is flexible and expandable. One advantage of the side branch 3 being flexible and expandable is that the side branch 3 is easily movable in at least one dimension independent of the movement of the main body 2 such that a branch vessel can be found and more easily aligned with during implantation to enter into with the side branch 3.

FIGS. 14A-D are a perspective view, a top view, a lateral view and a front view of an example of a modular covered stent 300 with a single lateral side branch. Alternatively, or in addition, the covered stent 1 may have more than one side branches 3, like covered stents 310, 320 shown in FIGS. 5a and 5b. Connection section 3a providing a degree of movement of branch 3. This improves long term stability and may contribute to prevent clot formation.

Alternatively, or in addition, the covered stent 1 has a plurality of legs and wherein at least one of the legs comprises a side branch 3. Thus, in an example (not shown) the covered stent 1 has a plurality of legs and each leg comprises a side branch 3. In an example the side branch 3 is deflated, collapsed or folded and may look like the side branch 3 of FIG. 3. Collapsed may include radially and/or longitudinally collapsed states, allowing reduced cross-section for delivery.

Figure 7:
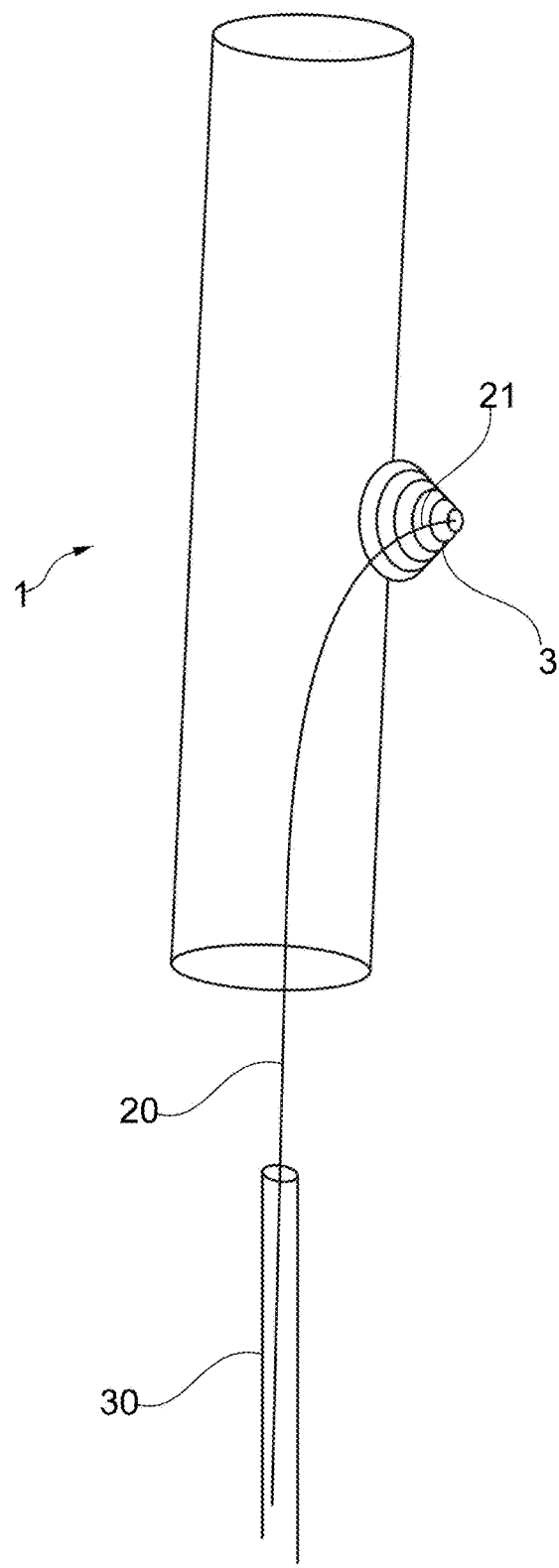
FIG. 7 is a schematic illustration of a covered stent with a folded or collapsed side branch be used to locate a branch vessel.

In an example the shape of the side branch 3 when collapsed may be dome shaped, or substantially half sphere shaped, see FIG. 7 for a non-limiting example. This allows the covered stent 1 to be safer for insertion during operation and/or navigation to a branch vessel than known devices of today since the side branch 3 does not have any sharp edges that can tear, rip or penetrate the branch vessel as known devices of today. However, the branch vessel 3 is preferably only longitudinally expandable from a min body 2 and cylindrical in shape, as e.g. shown in FIG. 1, 2, 4, 5a, 5b, 6, 8, 10, 11, 14, 15B,C, 20.

The side branch 3 is configured so that its shape may be changed to fit the branch vessel and allows for further extension away from the main body of the covered stent into the branch vessel with for example another covered stent or covered stent. Such expanded state includes in particular a longitudinally expanded shape of the branch 3, such as schematically illustrated in FIGS. 4, 5a, 5b, 9 and 10, 11, 14, 15,17, 19, 20. Transition from the longitudinally collapsed state to the expanded state may be done by unfolding, stretching, spring effect or other similar operations of the branch 3, as illustrated in FIG. 6.

Figure 5:
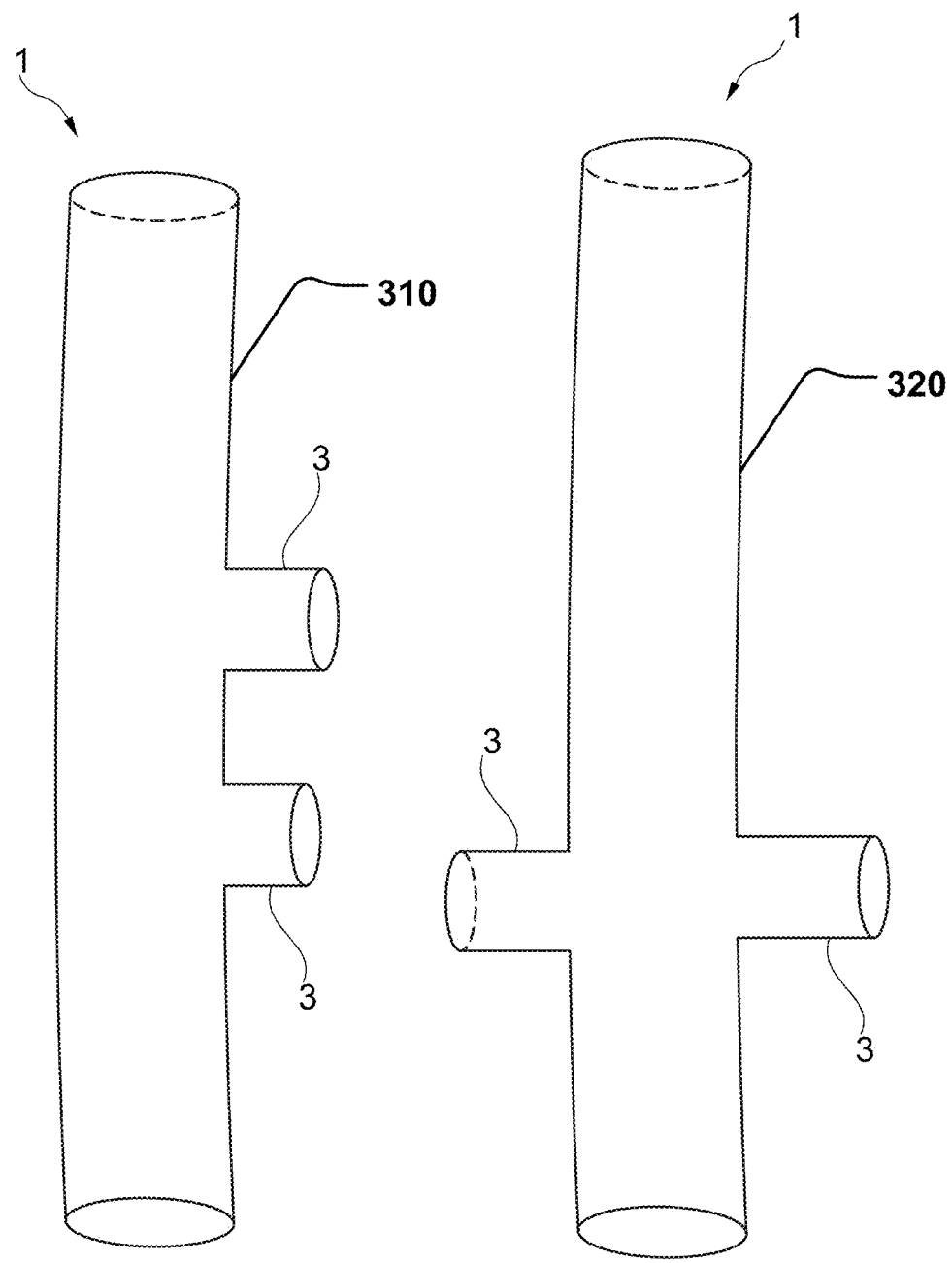
FIGS. 5a-b are a schematic illustrations of two examples of a covered stent with more than one side branch.
Figure 6:
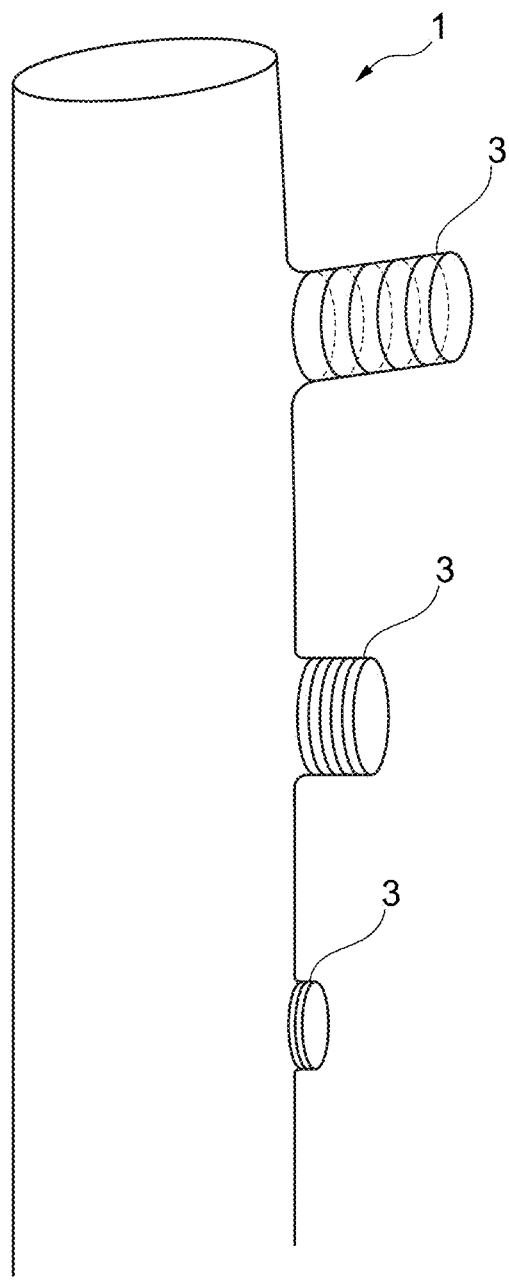
FIG. 6 is a schematic illustration of, bottom-top, one example of a side branch which is self-expandable from a collapsed to an expanded shape.

FIGS. 5a-b show two examples of a covered stent with more than one side branch in the expanded state. The covered stent 310 shown in FIG. 5a has two lateral side branches 3 protruding from the same side. The covered stent 320 in FIG. 5b also has two side branches 3, but they protrude from opposite sides.

Other configurations of side branches are provided as needed for anatomical reasons at a target site. In an example, the side branches 3 are distributed at any desired location on the main body 2. In an example the locations are based on the layout of the vessel wherein the covered stent 1 is going to be placed, and its side vessels. Although not shown, the covered stent 1 may also have more than two side branches 3. The side branches may have an angle inclined towards the side branch, i.e. an angle from the longitudinal axis of the main body other than 90 degrees, e.g. between about 30 or 45 to below 90 degrees.

As will be explained more, further below, the lateral side branch 3 may be expandable from a first protruding length or size to a second protruding length or size. This expansion may be independent of an expansion of the main body 2, or vice versa, the expansion of the main body 2 may be independent of the expansion of the side branch 3. This means that when the covered stent 1 with the side branch 3 is collapsed or folded, in one example the side branch 3 can be expanded or unfolded without the main body 2 of the covered stent 1 being expanded or unfolded. In another example the main body 2 of the covered stent 1 can be expanded or unfolded without the side branch 3 being expanded or unfolded.

As the side branch portion 3 of the covered stent 1 is in some embodiments flexible when extended, alignment with the side branch vessel can be less critical than with conventional covered stents. Thanks to the flexibility, navigation towards and/or into the side branch vessel is facilitated during implantation and when implanted by the flexibility of the side branch 3, illustrated in e.g. FIGS. 7 and 11. Some misalignment of the orifice of the side branch 3 at the main body of the covered stent 1 in relation to the branch vessel orifice may be corrected by the path of the flexible laterally extending side branch 3. A blood communication path of the side branch 3 can be extended by matingly engaging a further covered stent or covered stent graft interconnecting at the distal end of side branch 3 and extending into the side branch vessel.

FIG. 6 shows an illustration, bottom-top, of an example of a side branch which is self-expandable from a collapsed to an expanded shape. FIG. 6 illustrates one example of a covered stent 1. The covered stents discussed herein are in an example self-expanding, or in another example expandable by another device, such as an inflatable balloon, a pusher unit, or the like. FIG. 6 illustrates three different side branches 3 at different expansion lengths.

The covered stent 1 has a main body 2, which is a covered stent, and a lateral side branch 3 connected to the main body 2. The side branch 3 protrudes out from the main body 2 and is expandable and optionally flexible and/or tiltable in an angle relative the main body longitudinal axis and/or arranged in such angle when protruding from the main body 2. One advantage of the side branch 3 being flexible and expandable is that the side branch 3 is easily movable in at least one dimension independent of the movement of the main body 2 such that a branch vessel can be found and more easily aligned with during implantation to enter into the side branch 3.

In an example the covered stent 1 may have more than one side branch 3. In an example the covered stent 1 has a plurality of legs and wherein at least one of the legs comprises the side branch 3. Thus, in an example the covered stent 1 has a plurality of legs and each leg comprises a side branch 3. In an example the side branch 3 is deflated, collapsed or folded and may in an example look like the side branch 3 of FIG. 7. Collapsed may include radially and/or longitudinally collapsed states.

In an example the shape of the side branch 3 when collapsed is dome shaped, or substantially half sphere shaped, such as shown in FIG. 7. The above allows the covered stent 1 to be much safer for insertion during operation and/or navigation to a branch vessel than known devices of today since the side branch 3 does not have any sharp edges that can tear, rip or penetrate the branch vessel as known devices of today.

The side branch 3 is configured so that its shape may be changed to fit the branch vessel and allows for further extension away from the main body of the covered stent into the branch vessel with for example another covered stent or covered stent. Such expanded state includes in particular a longitudinally expanded shape of the branch 3, such as schematically illustrated in FIGS. 4, 5*a*, 5*b*, 6, 8, 9 and 10, 11, 14, 15, 17, 19, 20. Transition from the longitudinally collapsed state to the expanded state may be done by unfolding, stretching, spring effect or other similar operations of the branch 3, as illustrated in FIG. 10.

Figure 10:
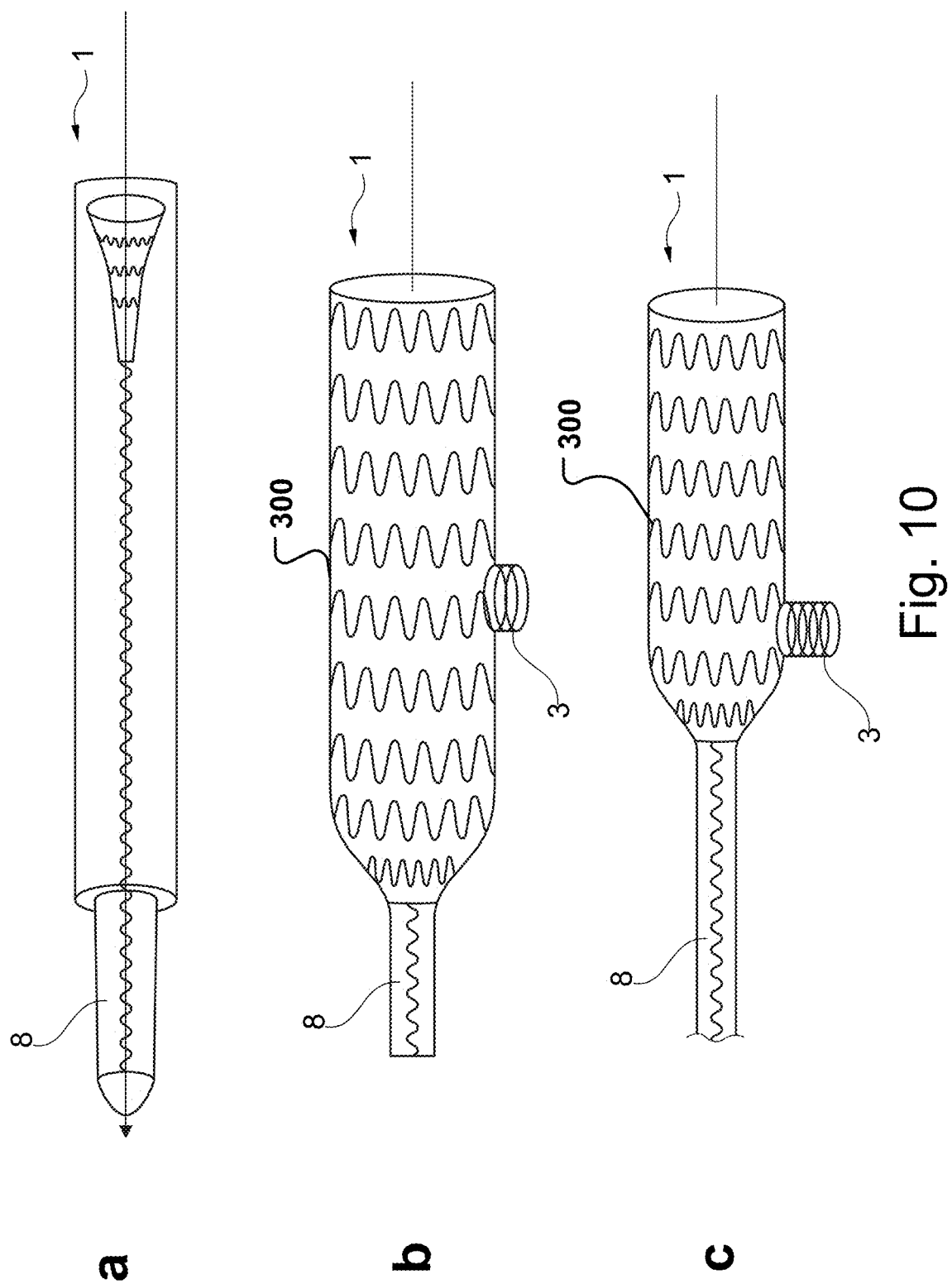
FIG. 10 is a schematic illustration of a sheath used to hold the covered stent in a collapsed or folded manner, and to controllably release the covered stent, partially or fully.

In an example expansion may be obtained by a spring effect of the covered stent 1 and/or the side branch 3, as e.g. illustrated in FIG. 10. The expansion may come to an equilibrium position within the vessel in an example.

The lateral side branch 3 is preferably integrally formed with the main body. The side branch is in some embodiments provided with a spring elastically self-expanding the side branch 3 in the longitudinal direction of the side branch 3 without radial expansion. The spring may be a helical spring wound as shown in the FIGS. 15B,C. A spring like structure can be preferably provided to help a side branch expand from the prosthesis main body, such as perpendicular to it, or alternatively at a different angle than 90 degrees from the longitudinal axis of the main body.

The covered stent 1 or side branch 3 may include wires that are suitably arranged as a stent/supporting frame part of the covered stent. In an example the wires may have a U shape in a longitudinal direction of the covered stent. In another example the wires may be helically wound, as illustrated in FIG. 10. In yet other examples they may be arranged in suitable patterns, like zigzag patterns etc.

In an example the wires may be wires interwoven with the covering. The wires may form a mesh, like a knitted pattern or a braiding. The wires may also be laser cut to form the springy pattern of the stent part.

Alternatively, or in addition, the wires or other expansile components of the present device may be made of a shape memory material. The shape memory effect of such wires may provide for a change of shape, such as collapsed to expanded shape, by means of known triggers like temperature. Suitable materials include Nitinol, CrMo alloys, shape memory polymers, etc. Shapes of components of embodiments made of such materials may be provided by heat treatment. Components of embodiments of such materials may rely solely on elastic or superelastic properties (e.g. Nitinol) for a change of shape from a collapsed or compressed configuration to an expanded, released, configuration.

When the covered stent 1 is made in a resilient configuration, upon exiting a delivery catheter, it will resiliently expand out from the main body of the covered stent, as for instance described below with reference to FIG. 10.

FIG. 7 illustrates how a covered stent with a folded or collapsed side branch can be used to find a branch vessel. The volcano shape of side branch 3, is as mentioned above only an example. A guide wire 20 is fed through the side branch and a catheter is thread over the guidewire. Then a delivery passage through the side branch is provided.

Guidewire 20 may be brought into place via a catheter 30 earlier guided by the guiding element 10 to the target site, e.g. at the side branch 3. Catheter 30 may be retracted and a different catheter be threaded over the guidewire thus put in place by means of guided catheter 30.

FIG. 8 illustrates a covered stent 300 with a side branch 3, and a catheter with a guiding mate 9 for guiding the catheter 30 for easy navigation of the side branch.

In an example, illustrated in FIG. 8 the catheter 30 comprises a guiding mate 9 which is configured to run over the guiding element 10 and/or navigation element 20 when guided by the guiding/navigation element to the side branch 3.

Figure 16:
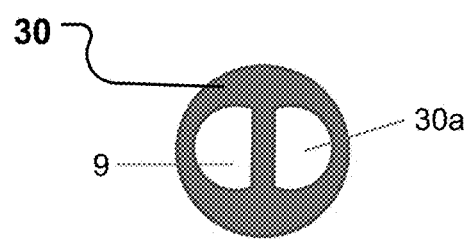
FIG. 16 is a cross sectional view of a double lumen delivery catheter.

In this example the guiding mate 9 is a length of tube attached to the catheter 30. Alternatively, the guiding mate 9 is integrally formed with the catheter, e.g. by suitable extrusion of the tubular member of the catheter. The guiding mate may be formed as an inner lumen, and/or integrated with the catheter wall. The guiding mate 9 may be integral with the catheter, or alternatively a separate element suitably attached to the guiding element 10, e.g. by adhesion, welding, or other mechanical attachment means. The catheter 30 may be a multi lumen catheter with at least one lumen. Preferably, it is a double lumen catheter. An example is schematically illustrated in FIG. 16. A first lumen 30*a* is provided for delivery of a unit, deployable through the distal orifice of the first lumen. A second lumen, as guiding mate 9, is provided for threading over the proximal end of the guiding element 10 towards the distal end and attachment point thereof as described above. The second lumen has preferably an orifice provided proximally of the distal orifice of the first catheter lumen. In this manner, the distal orifice of the first lumen is positionable distally beyond the attachment point of the guiding element 10.

Alternatively, or in addition, the guiding mate 9 comprises a ring, eyelet, snarl, or loop for threading through of the guiding element 10. An inner diameter of the guiding mate 9 is matched to receive an outer diameter of the guiding element 10 with some tolerance to avoid too much friction between the two elements for sliding motion along each other.

The guiding mate 9 is a unit for matingly receiving the guiding element 10 there through for being slidingly movable along the guiding mate 9 to and from the guiding mate's distal end where it is preferably attached to a covered stent. The guiding element 10 is configured to be threaded through the guiding mate 9 for being slidingly moveable along the guiding mate 9. Threading through of the guiding element 10 is suitably done outside of the patient at the proximal end of the guiding mate, e.g. a suture, thread, filament or wire, of e.g. multifilament strands, that are for instance braided together, to form a flexible guiding unit 10.

Alternatively, or in addition, the guiding mate 9 can be a lumen of a dual (or multi) lumen catheter or any other suitable element which is configured to allow sliding on the guiding element 10 and preferably does not damage the vessel or lumen it is used in.

The guiding mate 9 has advantageously a distal end or opening which is arranged a suitable length remote, i.e. proximal, of the distal end of the catheter 30. In this manner, the distal end or opening of the catheter 30 may advance further distally than the guiding mate 9 when at the end position of the guiding element 10 and/or navigation element 20, e.g. at a fixation point, such as a knot of a suture, where the guiding element 10 and/or navigation element 20 is distally affixed to a covered stent, e.g. at an orifice or opening thereof as described and illustrated herein.

The guiding mate 9 has thus a distal end or opening which preferably is arranged at the catheter proximal (at a distance) of a distal end or distal opening of the catheter 30.

In this manner, it is ensured that the distal end of catheter 30 may be positioned distally of the connecting point 11 for instance enters a side branch into which a delivery is to be made through the lumen of the catheter, e.g. a covered stent into a side vessel and assembly as well as interconnection with a main vessel covered stent in which the fixation point is located. In this manner, the side vessel covered stent can be delivered to the right location, i.e. branch opening, of the main vessel covered stent with minimal X-ray dosage as no 3D visualization is needed for the operator.

In an example, also related to FIG. 8, a guiding element 10 is attached to the side branch 3. This allows any further elements to be implanted, preferably covered stents, to be easily delivered through a catheter 30 with guiding mate 9 for e.g. being connected to the side branch 3 or delivered out of a side branch 3 with minimal effort and improved reliability as well as patient safety.

As shown in FIG. 8, the guiding mate 9 is in some embodiments placed at a distance from the distal end of the catheter 30. One advantage with the guiding mate 9 at a distance from the distal end of the catheter 30 is that the catheter 30 may then reach further than the position 11 of the attachment of the guiding element 10. E.g. if the guiding element 10 is attached at the side branch 3, the catheter can reach further out through the side branch 3. This enables easy access for positioning and connecting e.g. an extension covered stent 600 at the side branch 3.

The distal end portion of the catheter 30, preferably distally of the guiding mate 9 distal end, can additionally, or alternatively, be bent, see FIG. 8. This allows for a desired exit angle of the orifice of the delivery catheter 30 at its distal end, for instance substantially perpendicular in relation to a longitudinal axis of a main body 300.

However, the guiding mate 9 distal portion or end may in some embodiments reach all the way up to the distal end of catheter 30. Improved, advantageous minimally invasive delivery of elements through a side branch is ensured in any case.

Figures 9A, 9B, 9C:
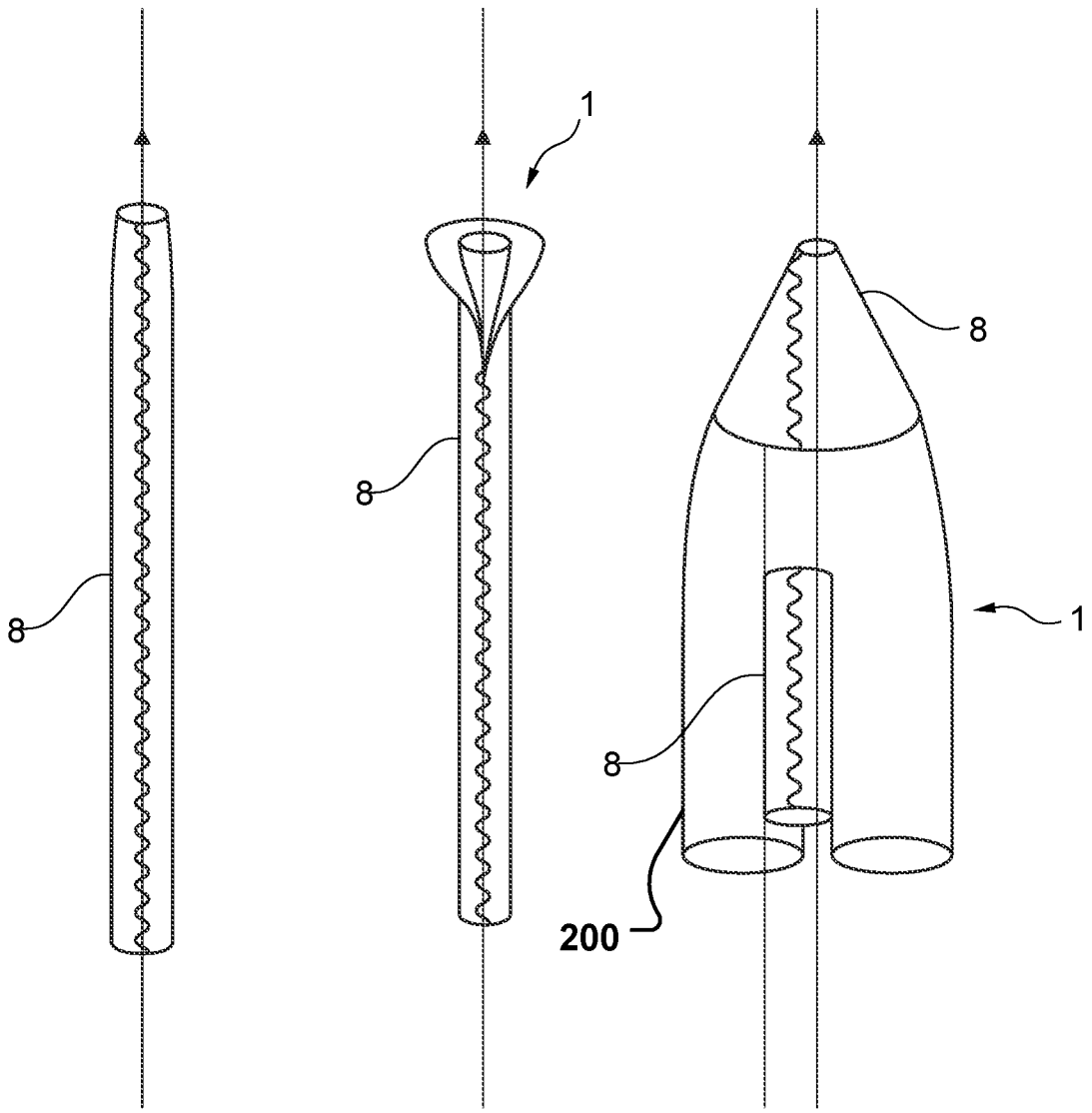
FIGS. 9a-c is a schematic illustration of a restraining member and a covered stent being self-expandable from a collapsed to an expanded shape by removal of the restraining member.

In an example, as illustrated in e.g. FIGS. 9a,b,c, 10 and 11, 15 and 17 the covered stent 1 is provided with a restraining member 8 that prevents the covered stent 1 from expanding until release of the restraining member provides for controllably expanding the covered stent 1.

In an example the restraining member 8 is made of a PTFE or Gore-Tex® material. The restraining member 8 ay be provided as a flat sheet, fabric or nonwoven material releasably arranged around a covered stent for delivery. Alternatively, any other suitable biocompatible materials may be chosen for the restraining member that can be inserted into the body and easily manipulated as well as protect any vessel or lumen from the covered stent 1 during deployment.

FIG. 9a-c illustrate an example of a restraining member. For instance a covered stent 200 that is self-expandable may be provided with such restraining member 8. The covered stent transitions controllably from a collapsed to an expanded shape by removal of the restraining member.

In an example, the removal of the restraining member 8 is done by simply pulling on a string which then releases a seam holding together a sheet of the restraining member 9 arranged around the covered stent. Pulling the release string unfolds the restraining member along the seam, depending on the distance pulled on the string. The restraining member unfolds thus partially or fully, as for instance illustrated in FIGS. 9a-c. In an example more than one string/seam is used to select where the restraining member 8 is removed from restraining the covered stent and/or side branch 3.

Alternatively, or in addition, the restraining member 8 is configured to be partially removable so that the expansion of the covered stent 1 and/or side branch 3 can be selected individually. This is illustrated in FIG. 9a, where the covered stent is fully restrained by the restraining member 8. In FIG. 9b the restraining member 8 is shown as partly opened and thereby allowing the covered stent to partially expand. Partially expanded stent may still be repositioned if so desired.

The example illustrated in FIG. 9c shows more than one restraining member 8 for restraining portions of a covered stent. Each restraining member is thus provided for restraining different parts of a covered stent, here in the example the three-legged covered stent 200. In this way, the three legs can easily be expanded individually, one at a time or simultaneously. In the same manner a covered stent 1 with a side branch 3 can be partially or fully expanded by releasing it from e.g. a restraining member around the main body 2 and another restraining member 8 around the side branch 3. An example is described below with reference to FIG. 18.

The collapsed unit (FIG. 9a) is introduced to a target site through a delivery catheter that may have a guiding mate 9 slidable along a guiding element 10 as described above. The assembly shown in FIG. 9 (and similar others) may include one or more guiding mate(s) 10 itself, as e.g. shown in FIG. 3. The latter guiding element(s) 10 are led outside from inside the restraining member 8 from the covered stent (here 200), and further proximally towards the proximal end of the catheter, outside the patient. Thus further elements may advantageously be delivered through the covered stent when implanted, as described herein.

In an example more than one string is used to select where the restraining member 8 is removed from the covered stent 1 and/or side branch 3.

Alternatively, or in addition, the string of the seam of the restraining member is one of guiding element(s) 10 when attached to the covered stent 200. The guiding element then 10 is attached distally to the covered stent, as e.g. in FIG. 3, runs proximally out of an orifice of the covered stent 200. Then it is folded back, runs inside the protection unit 8. Turning back proximally again, it provides the releasable seam. When pulled and removed from the seam, i.e. the restraining member is released, it is further pulled back, leaving a guiding element 10 for use as a catheter guide. This synergetic guiding element 10 and seam of a protective unit/restraining member 8 is advantageous in that the number of components is reduced that needs to be drawn outside of the patient, amongst other advantages. The restraining member 8 is configured to be partially removable so that the expansion of the covered stent 1 and/or side branch 3 can be selected individually. This is illustrated in FIG. 9a, where the covered stent 200 is fully restrained by the restraining member 8. In FIG. 9b the restraining member 8 is partly opened and thereby allowing the covered stent 200 to have partially expanded, here along its length.

Another example is illustrated in FIG. 9c, where more than one restraining member 8 is used to restrain different parts of the three-legged covered stent. In this manner, for instance one or more of the three legs of covered stent 200 can easily be expanded individually, one at a time or simultaneously. In the same manner a covered stent 1 with a side branch 3 can be partially or fully expanded by releasing it from e.g. a restraining member around the main body 2 and another restraining member 8 around the side branch 3 (not shown)

FIG. 10 illustrates how a sheath may be used to hold the covered stent in a collapsed or folded manner, and to controllably release the covered stent, partially or fully.

FIG. 10 illustrates how the covered stent 1 is first released from restraining member 8 from one side, the right hand side as shown in the top part (a) of FIG. 10. As illustrated in the middle and bottom parts (b and c) of FIG. 10, the part of the covered stent 1 that comprises the side branch 3 is then released. This is further illustrated in FIG. 11, where the covered stent 300 is partly released from the restraining member 8 to allow easy fitting of the side branch 3 with a branch vessel. When the part of the covered stent 300 that comprises the side branch 3 is released from the restraining member 8, the side branch 3 is aligned with the branch vessel and is then expanded into the branch vessel. The covered stent 300 is then fully released from the restraining member 8, as illustrated in the bottom part of FIG. 11. A covered stent 600 extending further into the side vessel is shown delivered and deployed as described herein.

Figure 11:
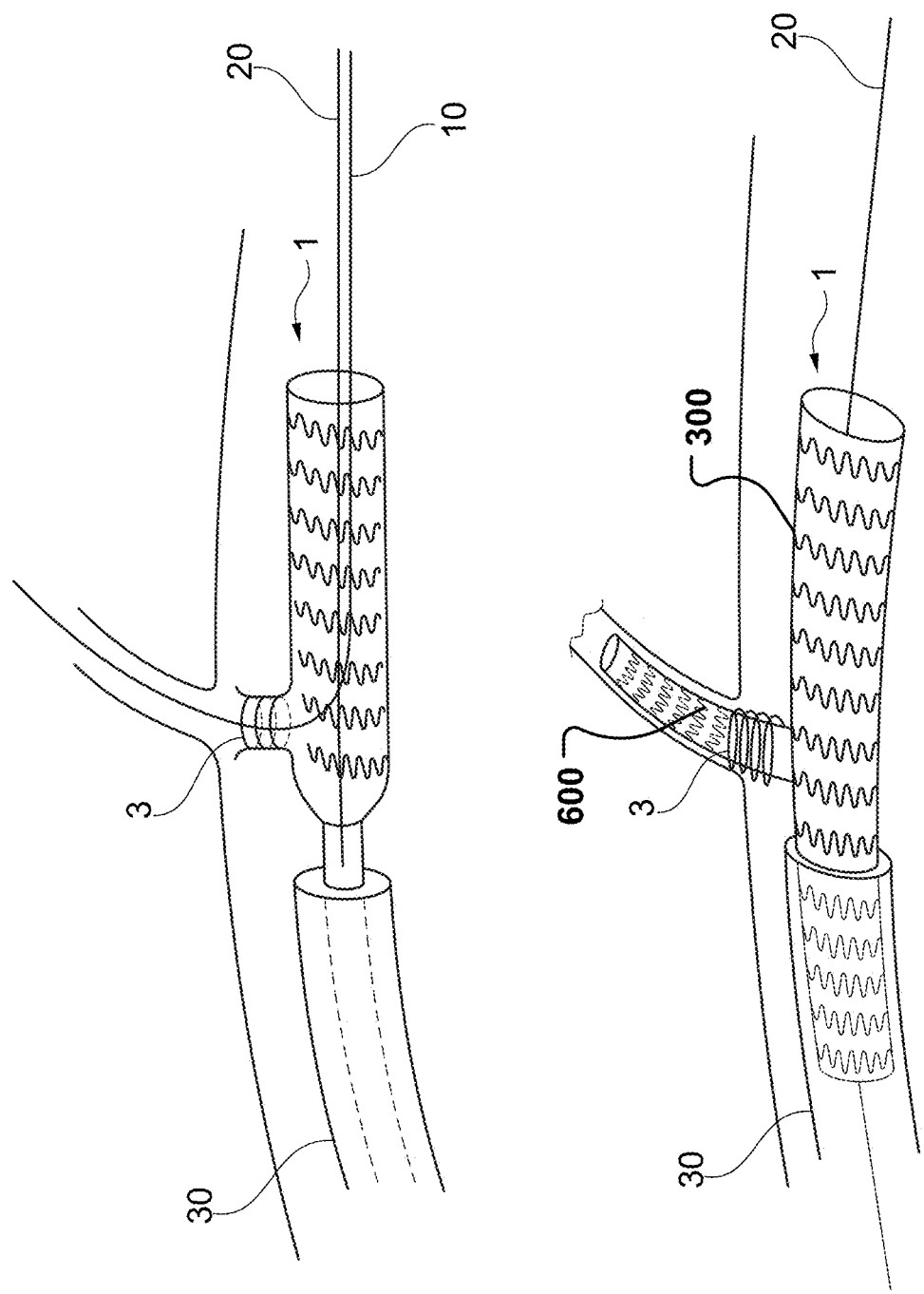
FIG. 11 is a schematic illustration of a covered stent before and after the covered stent is fully expanded.
Figure 14A:
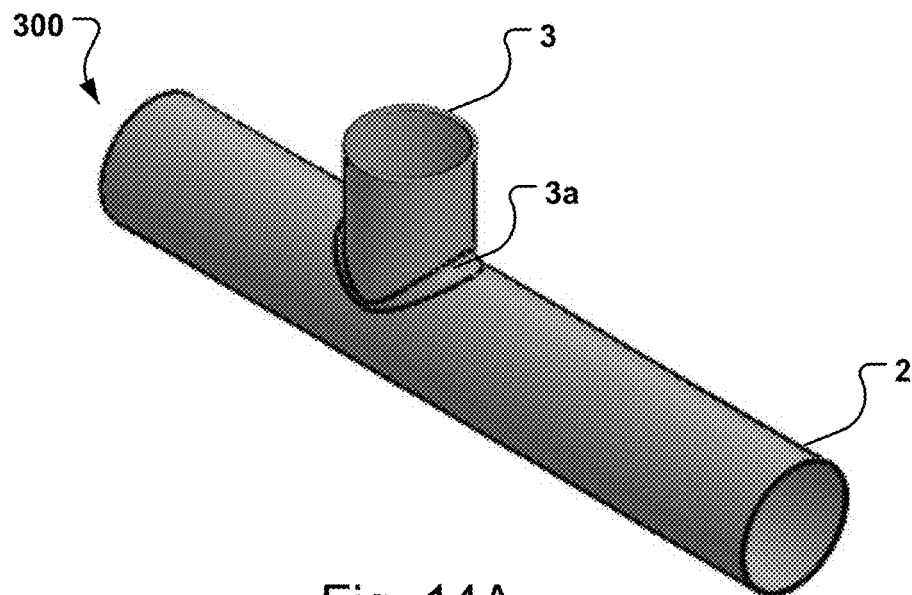
FIGS. 14A-D are a perspective view, a top view, a lateral view and a front view of an example of a modular covered stent 300 with a single lateral side branch.
Figure 14B:
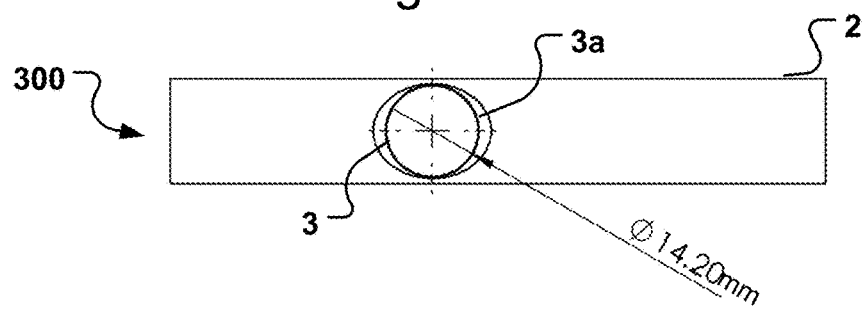
Figure 14C:
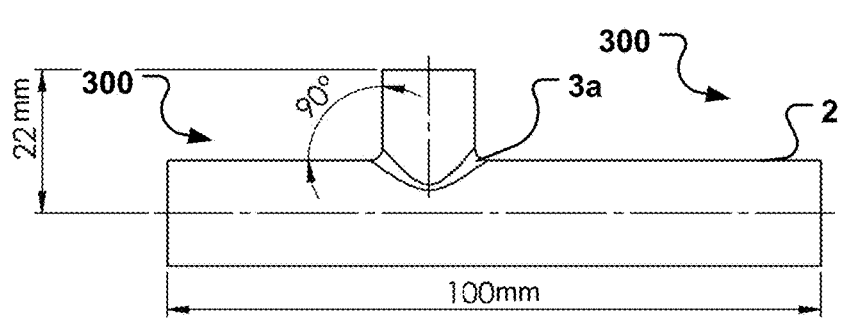
Figure 14D:
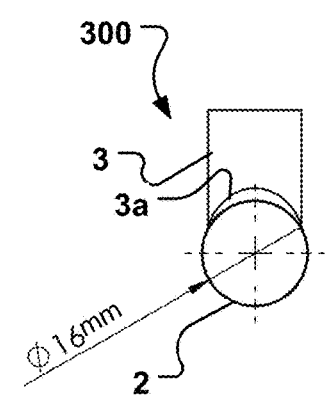

FIG. 11 illustrates an example of a covered stent 1 which can be used in an easy method of finding a branch vessel. The covered stent 300 is pushed fully out of a delivery device 30, such as a catheter, and the main body 2 of the covered stent 1 is expanded.

The side branch 3 is in examples expanded by pushing it outwards and/or configured to expand by itself, as disclosed above and illustrated in e.g. FIGS. 6, 7 and 9.

A further pushing element (not shown) can used to push the flexible side branch 3 in a desired direction and outwards, so that it expands from a folded or collapsed state. This applied in case the side branch 3 is not self-expandable.

In case of a self-expandable side branch 3, it will expand radially outwards from the main body as soon as it is released from the delivery catheter (30), and/or a restraining unit 8 is removed.

For easier alignment with a branch vessel, the covered stent side branch 3 can be provided with a marker 21, as e.g. illustrated in FIG. 3. The marker 21 will make it visible to the operator when the side branch 3 is level or aligned with a branch vessel. By having only one marker at the side branch 3 it will be easier for the operator to align the covered stent 1 to its desired location by use of an imaging device, such as X-ray, than today's covered stents having a plurality of markers that need to be brought in alignment in fluoroscopy. The marker 21 is in examples any fiducial marker visible under common type if imaging devices used in healthcare or covered stent placement such as MRI, X-ray, Ultrasound, and so on. Covered stent structures usually are themselves difficult to see under e.g. fluoroscopy. Markers may e.g. made of gold or similar materials allowing good visibility in such imaging.

In an example, the side branch 3 is folded or collapsed and restrained by a guide element 10, such as a suture 10. The guiding element 10 is for instance wrapped around the side branch 3, and is releasable connected on the inside of the side branch 3 or otherwise attached to the side branch 3 causing it to be releasably folded or collapsed. Pulling the guiding element proximally then releases the side branch 3 from the collapsed state to the expanded state. Guiding element 10 remains in place for use as a catheter guide.

In an example the covered stent 1 is aligned with a branch vessel by moving the main body 2 of the covered stent 1, as e.g. illustrated in FIGS. 9-11. In an example, this is achieved by the covered stent 1 only being partially pushed out of the catheter 30 and/or partially freed from the restraining device 8 as also disclosed above, so that the covered stent 1 can be moved by moving the catheter 30, or otherwise moved by e.g. a pusher wire, e.g. illustrated in FIGS. 9 and 10. Preferably, the side branch 3 is self-expandable.

In an example, the covered stent 1 is moved upwards until the marker 21 on the side branch 3 aligns with the branch vessel. Then the covered stent 1 is rotated until the side branch 3 enters the branch vessel. When the side branch 3 has entered the branch vessel the guiding element/e.g. suture 10 is released, allowing the side branch 3 to expand into the branch vessel, either by itself or by pushing it outwards.

In a further alternative example, the covered stent 1 is aligned with a branch vessel by navigating both the main body 2 of the covered stent 1 and by navigating the side branch 3 of the covered stent 1.

Figure 15A:
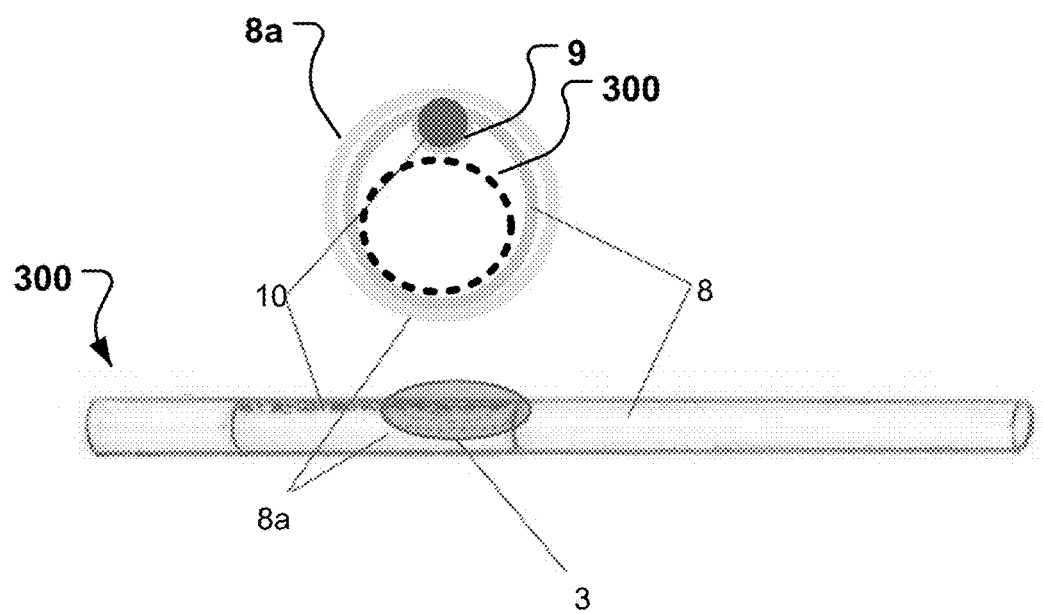
FIG. 15A is a perspective and sectional view (upper part of figure) of a modular covered stent 300 with a lateral side branch in a delivery configuration in a perspective view (lower part of figure)
Figure 15B:
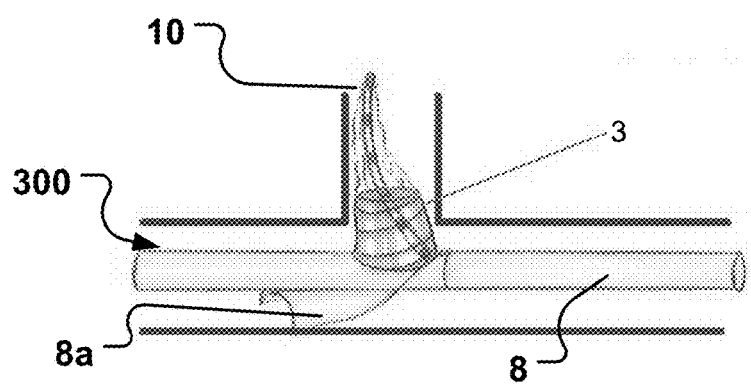
FIGS. 15B and 15C are schematic views of deployment of the lateral side branch of the modular covered stent 300 of FIG. 15A before release of the main body.
Figure 15C:
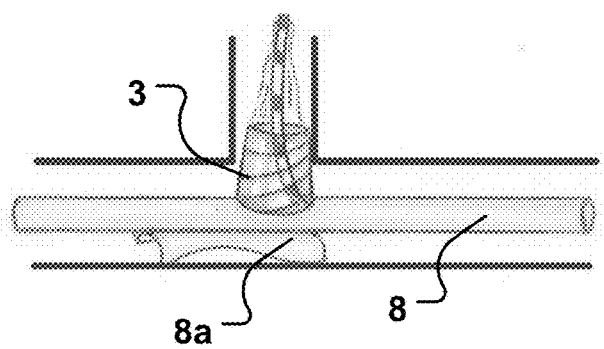

FIG. 15A is a perspective and sectional view of a modular covered stent 300 with a lateral side branch in a delivery configuration. FIGS. 15B and 15C are schematic views of deployment of the lateral side branch of the modular covered stent 300 of FIG. 15A before release of the main body. There are two layers of outer restraining members/sheath that cover the prosthesis/covered stent. A side branch outer restraining member 8a to restrict the side branch prosthesis only. It wraps outside of a first outer restraining member 8. It is only about a portion, such as ⅓ of the length of the entire prosthesis. The first outer restraining member 8 covers the entire body of the prosthesis with a shape cut out on it to allow the side branch prosthesis to pop out. The side branch outer restraining member 8a will be opened first to release side branch guidewire and side branch prosthesis. Once the side branch vessel is located, the first outer restraining member 8a can be opened to fully expose the prosthesis main body, as is illustrated in FIGS. 15B and 15C. The prosthesis delivery system is inserted and lined up with the side branch tip close to or directed towards the side branch vessel. The position of the prosthesis is adjusted if needed, e.g. by the help of fiducial markers, optionally a guidewire can be used to find the side branch entrance. The side branch outer sheath 8a is opened. The side branch outer sheath 8a can be opened fully to release the side branch prosthesis. The side branch prosthesis fully expands. Then the prosthesis main body outer sheath 8 is opened to release the entire prosthesis. A two lumen catheter 30 can be brought over the guiding element 10 to bring another guidewire into the side branch for the connecting prosthesis delivery system. One of the lumens 9 will go over the side branch guide element 10 to gain access to the side branch vessel. Once the two lumen catheter 30 is in place, another guidewire will be introduced to the side branch through lumen 30a which can be freely move upwards for deeper access as described in more detail with reference to methods and procedures below.

Figure 17A:
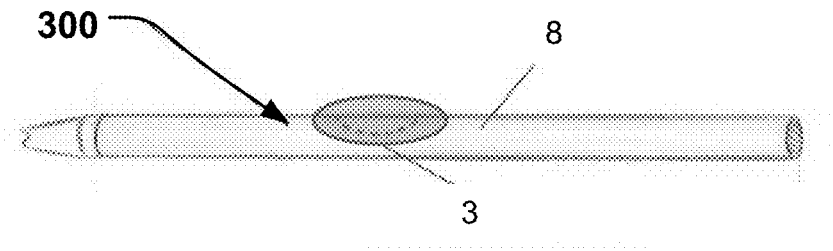
FIG. 17A is a perspective and sectional view of a modular covered stent 300 with a lateral side branch in another delivery configuration.
Figure 17B:
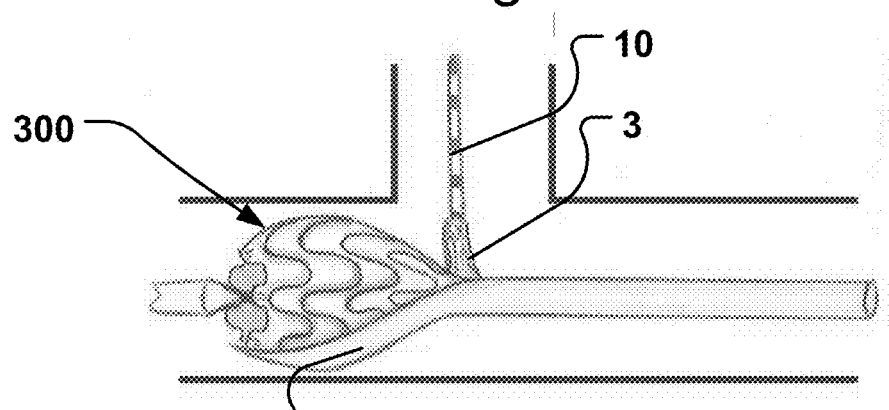
FIG. 17B is a schematic view of a release of a main body and lateral side branch of the modular covered stent 300.
Figure 18:
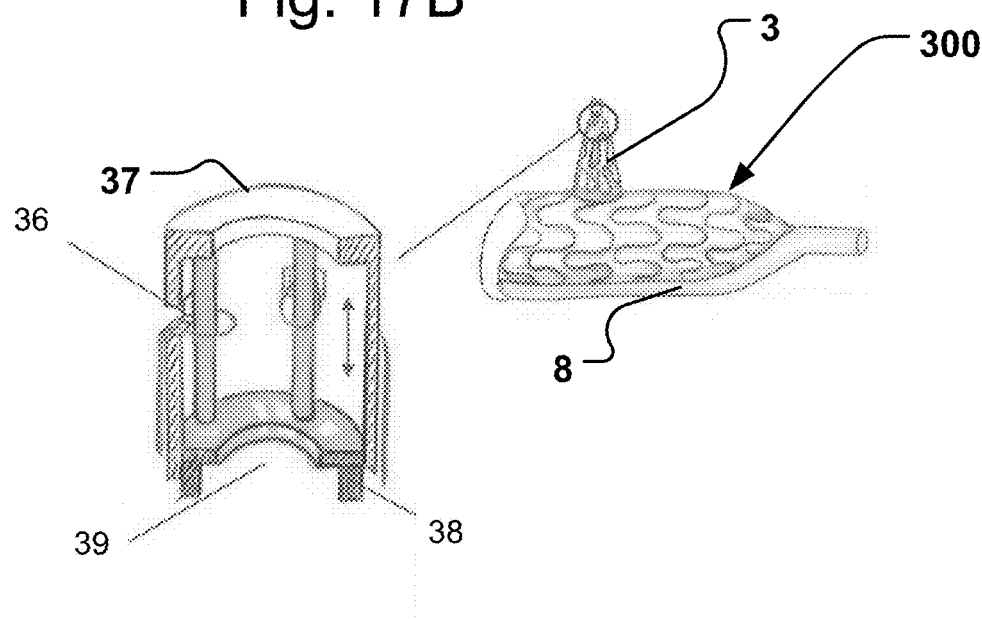
FIG. 18 is a schematic view of a catheter tool for releasing a navigation unit from an extension of a lateral side branch.

FIG. 17A is a perspective and sectional view of a modular covered stent 300 with a lateral side branch in another delivery configuration. FIG. 17B is a schematic view of a release of a main body and lateral side branch of the modular covered stent 300. FIG. 18 is a schematic view of a catheter tool for releasing a navigation unit from an extension of a lateral side branch.

There is a single layer of outer sheath 8 covers the entire prosthesis/covered stent. The prosthesis exposure can be divided into three stages:

First stage: The distal section of the outer sheath 8 is opened, releasing about ⅓ of the prosthesis main body. The outer sheath 8 is opened slowly to release the first section of prosthesis main body. Adjust the position of the prosthesis can be done.

Second stage: The outer sheath 8 is opened continuedly till the side branch prosthesis 3 is fully exposed. Once the correct position is found, the mid section of the outer sheath 8 is opened to release the side branch 3. The side branch 3 is expanded. The outer sheath 8 is further opened till the side branch 3 prosthesis is fully exposed and adjust its position if required. To open the tip of the side branch prosthesis, loops provided are released from a bar that is holding it. Once the loops are released from the locking mechanism, the covered stent will expand resiliently and/or by shape memory effect. The outer sheath 8 is continuedly opened till the main body 2 is exposed. Now, surgeon can deliver an expansion covered stent 600 to the side branch vessel. Expanding a section of the prosthesis main body 2 before launching the side branch potentially may help the surgeon on placing the guide wire in the side branch vessel.

The last stage: Till the side branch prosthesis is in the side vessel, the sheath 8 is fully opened.

FIG. 18 is a schematic view of a catheter tool for releasing a navigation unit from an extension of a lateral side branch. The distal end of the catheter 30 lumen may include a distal unit for releasable attachment of a branch 3. Branch 3 may for instance include attachment means like loops 35. The attachment means like one or more wire or thread loops 35 are attached with the prosthesis side branch 3 distal end and can be releasably fixed to a locking part 38. The locking part 38 can for instance be moved up or down relative a stop unit like the flange at the distal end shown in FIG. 18. The locking part may include one or more rods or struts longitudinally movable and engageable with the loops 35. The locking part 38, like including the rods or struts, can be releasably locked with the attachment means like the loops 35, e.g. when moved up to the stop flange, such as shown. Release of the locking unit to the attachment means may be provided by reversing the movement of the rod(s) in the opposite direction so the branch 3 is released and the catheter can be withdrawn proximally. A Central space 39 is provided for passing a guidewire or covered stent there through. In this manner, the branch 39 can be moved by moving the catheter end with the locking unit when attached to the branch. Movement is preferably towards the branch vessel, away from the main body but may also be provided to withdraw the branch 3 towards the main body if desired to adjust to the anatomical situation. The catheter may be guided with guiding element 10 as described above.

An example of a side branch prosthesis 300 implementation can be as follows:

Length of prosthesis side branch 3 may be approx. 15 mm

Some other exemplary but not limiting measures are given in FIG. 14

The pre-load guide element 10 feature:

It is secured with the side branch, preferably in a position that assists to manipulate the orientation of the catheter to matingly engage the guide element 10. The connection point is e.g. at the distally oriented inner side of the branch 3 such that the guide catheter 30 can be advantageously navigated through the lumen of the branch 3 towards a side vessel orifice or lumen.

The pre-load guide element 10 works as a guilder for a catheter 30, e.g. the double lumen catheter shown in FIG. 16 to reach the side vessel.

The pre-load guide element 10 is preferably configured to unlock from the prosthesis easily.

An example of a visceral side branch 310 can be as follows:

The prosthesis side branch 3 can be provided to maintain a certain angel in relation to the main body 2 longitudinal axis, e.g. approximately a 30-degree angle or a 45-degree angle to assist a surgeon to enter a side vessel with the catheter 30.

The inner diameter of a side branch may be in the range of about 7 mm,

The side branch prosthesis 3 is provided to allow a certain level of movement to allow adjustment to various connection angles towards side vessels.

FIG. 12 shows flow charts of two examples of a medical procedure.

The method 700 comprises the steps of accessing 710a target site being a vessel in a patient; delivering 720 a first covered stent to the inside of the vessel at the target site through a delivery catheter, wherein the target site has a side branch vessel; delivering 730 a second covered stent to the first covered stent; connecting 740 the first covered stent to the second covered stent for providing a blood flow to the side branch vessel. The delivery of the second covered stent includes sliding a catheter 30 along a guiding element 10 to a position inside a lumen of a side branch of the first covered stent; and expanding the second covered stent for connecting to the first covered stent. The catheter 30 with guiding mate 9 can be used for the delivering of a guide wire. Once the guidewire is in place in the side branch and extends sufficiently long into the side vessel at the side branch, the catheter 30 may be retracted. A covered extension stent 600 can then be delivered over that guidewire to the side vessel.

Alternatively, or in addition, the method 800 is provided. The second covered stent may have a side branch 3. The method includes delivering a second covered stent to a side vessel through a side branch 3 of the first covered stent. The method 800 comprises the steps of accessing 810 a target site being a vessel in a patient; delivering 820 a first covered stent to the inside of the vessel at the target site through a delivery catheter, wherein the target site has a side branch vessel; expanding 830 the side branch 3, delivering 840 a second covered stent to the first covered stent and through the side branch 3 to the side vessel; connecting 850 the first covered stent to the second covered stent for providing a blood flow to the side branch vessel. A catheter 30 with a guiding element 10 can be used between steps 830-840 as described above.

In a specific example the method includes delivering and assembling the system 100 as explained above and with a final layout illustrated in FIGS. 1 and 2.

The method starts in the example with soft guidewire being inserted into a vessel of a patient. Using a soft guidewire ensures that no part of the vessel is damaged during insertion. Further, the soft guidewire can be bent and thereby be navigated through the vessel system of the patient to a target site, here in the example the ascending aorta. As explained above other target sites in the body could also be chosen as an alternative.

Then, a first catheter is inserted, over the soft guidewire, into the vessel of the patient and navigated until it reaches the target site. Guided by the first catheter, a stiffer navigation element 20 is then inserted into the catheter and thus vessel of the patient.

The target site in the example is the ascending aorta where the three legged covered stent 200 is then positioned via the delivery catheter in the aortic arch. The delivered state, assembled with further components in the aortic arch is illustrated in FIG. 2.

Then a three-legged covered stent 200 is collapsed or folded to fit inside the first catheter 30 and pushed along it with the navigation element/guide wire 20 may running inside the main part of the covered stent and extending out through one of the legs 201.

The three-legged covered stent 200 is provided with a guiding element 10 attached inside one of the other legs, as described above. In an example a location near or to the left of the aortic arch is preferred.

Each guide element 10 and navigation element 20 can be labelled at the end proximal end for easy identification. The proximally labelled end is configured to be outside of the patient during implantation.

Following, when at the correct position of the target site, the covered stent 200 is pushed out of the catheter 30 and allowed to fully or partially expand or unfold, as discussed above. It is rotated until the legs match the main vessel and the neck branch vessels of the aorta. And as explained above this alignment can be performed in various ways.

Next, when the three legged covered stent 200 is in place, the system 100 can easily be built up with further modules. As discussed above this can be done in several ways and in this example two covered stents 1 having side branches 3 and covered stents 600 for extending into the branch vessel are deployed following the three-legged covered stent 200 as described above with reference to FIGS. 1 and 2.

In the example illustrated in FIGS. 1 and 2 an extension covered stent 600 is navigated via the guide element 10 attached inside one of the legs of the three-legged covered stent 200 and navigated through the three-legged covered stent 200 and positioned so that it can extend out through the leg. Here the covered stent 200 is expanded and connected to the leg in an overlapping manner.

Following, the first covered stent 300 with the side branch 3 is slid into place along the guide element 10 and connected to the third leg 203. After or before the deployment along the guide element 10 the second covered stent 300 is slid along the guidewire 20 and connected to the second leg 202.

No aortic clamping stopping blood flow in the aorta or cardioplegia is necessary. Blood flow through the aorta and the side vessels is not interrupted during the procedure thanks to the parallel arrangement of the covered stents 300.

When delivering a covered stent the side branch(es) 3 are at the same time navigated into place with the covered stent and expanded into, or at least towards the branch vessel. Following, any additional extension covered stent can be inserted based on the desired need to further extend into the branch vessel.

Next, a covered stent 400 with two legs is moved in a collapsed state inside the first catheter 30 along guide wire 20 and guide element 10. The covered stent 400 is oriented so that the legs are positioned towards the covered stents 300 already connected. Each leg is guided along one of the guide element 10 and the guide wire 20, so that each leg can be guided to one of the previous covered stents 300 with side branches 3. When in place, the covered stent 1 is released from the catheter 30 and allowed to expand.

Alternatively, the collecting covered stent 400 may be connected to the proximal end of the branched covered stent 300 prior to connecting the side branch and/or delivering an extension covered stent 600.

Next a tubular shaped covered stent 410, without legs or side branches, is pushed into place through the catheter 30, and navigated and connected to the previous covered stent 400 in a similar manner but now having both the guiding element 10 and the guide wire 20 running inside. Length of the assembled prosthesis is adjustable by a variable overlap of the covered stents chosen by the surgeon during implantation when the interconnection of these is made.

Then a two-legged covered stent 420 is connected to the tubular shaped covered stent 1 in the same manner. This two-legged covered stent 420 is oriented with the legs away from the covered stents already distally connected upstream the aorta. These legs run along the guiding element 10 and the guide wire 20, respectively. The length of the assembled prosthesis is adjustable by a variable overlap of the covered stents chosen by the surgeon during implantation when the interconnection of these is made.

After connection of the two-legged covered stent 420, a covered stent 310 with two side branches 3 is guided along the guiding element 10 through a delivery catheter, in a manner similar to previously delivered covered stents 300. When the main body of the covered stent is in approximately the right place, further navigation of the side branch 3 is done to be rotationally correctly oriented towards the side vessels. The side branches 3 are thus aligned with the branch vessels and expanded into the branch vessels. Distally, the covered stent 310 is connected with one of the legs of the two-legged covered stent 420.

Then, a covered stent 320 with two side branches 3, and further guiding 10 or navigation elements 20, is guided via the catheter 30, aligned with branch vessels and connected to the second leg of the two-legged covered stent 420.

Finally, a last two-legged covered stent 430 is positioned and the two legs are connected to the two covered stents 310, 320 with two side branches 3, in a similar manner as described above, by use of a delivery catheter 30 and running along the guiding element 10 and the guide wire 20, respectively.

When the system 100 is connected and complete, all remaining navigation elements 20 and catheters 30 are removed from the patient. Guide elements 10 may be distally cut and remaining length left in place, preferably for subsequent biodegradation.

In an example, illustrated in FIG. 2, a complete system 100 is shown assembled and implanted inside an aortic arch of a patient. As can be seen, the different covered stents 1 have been connected to each other and side branches 3 have been extended into branch vessels and further extended with covered stents 1.

Further proximal covered stent modules (not shown), e.g. for iliac artery reconstruction or repair, may be provided and implanted, such as connected to the proximal end of the covered stent 430.

FIG. 13 illustrates a method for navigating a covered stent 1 to a branch vessel. The method 900 comprises the steps of providing 910 the covered stent 1, as discussed above, and navigating 920 the lateral side branch 3 into a branch vessel by moving the lateral side branch 3.

In an example this is performed by using an elongated navigation element 20, as also discussed above. In one example it is performed using a guide element 10 and a catheter 30 with a guiding mate 9, as described in relation to FIG. 8.

The method may further comprise the step of expanding the lateral side branch 3 from a collapsed state into the branch vessel when navigated to the desired position at the branch vessel. As described in relation to e.g. FIGS. 9-11, this may be done by navigating the covered stent 1 so that the side branch 3 is aligned with a branch vessel, then expanding the side branch 3 into the branch vessel, and finally expanding the rest of the covered stent 1.

In an example the method further comprises the step of interconnecting an expansion element at the lateral side branch 3 and into the branch vessel for further extension into the branch vessel. The expansion element may be a covered stent 1.

Further examples of methods and procedures are given below:

A method is provided for navigating a covered stent to a branch vessel. The method includes providing a covered stent 200, 300, 310, 320 and navigating the lateral side branch into or towards a branch vessel by moving the lateral side branch using a guide element 10. The method may include expanding a covered stent delivered through the lateral side branch 3 from a collapsed state into the branch vessel when navigated in position at the branch vessel. The method may include interconnecting an expansion element 600 at the lateral side branch and into the branch vessel for further extension into the branch vessel, wherein the expansion element preferably is a covered stent.

A method is provided for interconnecting a plurality of covered stents. The method includes providing a covered stent having a bendable guiding element connected at an exit of a side branch. The method may include interconnecting a plurality of such covered stents including sliding a catheter by means of a guiding mate 9 along the guiding element to the exit of the side branch and delivering another covered stent through the catheter along the bendable guiding element for interconnection of covered stents. The covered stents preferably have a same dimension at the interconnection.

A medical procedure is provided including accessing 710 a target site being a vessel in a patient; delivering 720 a first covered stent to the inside of the vessel at the target site through a delivery catheter, wherein the target site has a side branch vessel; delivering 730 a second covered stent to the first covered stent; connecting 740 the first covered stent to the second covered stent for providing a blood flow to the side branch vessel, wherein the delivery of the second covered stent includes sliding a catheter along a guiding element 10 to a position inside a lumen of a side branch of the first covered stent; and expanding the second covered stent for connecting to the first covered stent.

A medical procedure is provided including accessing 810 a target site being a vessel in a patient; delivering 820 a first covered stent to the inside of the vessel at the target site through a delivery catheter, wherein the target site has a side branch vessel; expanding 830 the side branch 3; delivering 840 a second covered stent to the first covered stent and through the side branch 3 to the side vessel; and connecting 850 the first covered stent to the second covered stent for providing a blood flow to the side branch vessel.

Another example of a delivery procedure is as follows:
1. Inserting a delivery system via an introducer sheath into a patient's body.
2. Opening an outer sheath 9 and removing from a proximal end of a prosthesis towards a side branch prosthesis direction. Keep opening till the side branch prosthesis is released and expanded fully.
3. Stopping opening till the side branch prosthesis is fully exposed.
4. Adjusting the position of the prosthesis for initial matching.
5. Inserting a double lumen catheter 30 over a pre-loaded guide element 10 and allow it travel to the side branch prosthesis, till it hits the end at connection point 11.
6. Insert an additional guidewire via the double lumen catheter 30 and make it protrude from the side branch 3.
7. Optionally performing further adjustment of the position of the prosthesis.
8. Once the position of the side vessel is identified and confirmed, advance the additional guidewire forward to secure the position.
9. Once the additional guidewire is securely staying in the side vessel, remove the double lumen catheter and deliver the connecting prosthesis 600 by using the additional guidewire.
10. Once the connecting prosthesis 600 is in side vessel and fully expanded, remove the rest of the outer sheath 9 of the previous prosthesis releasing it entirely.
11. Unlock the guiding element 10 from the side branch prosthesis and remove all guidewires and delivery system from the patient's body.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

The invention claimed is:

1. A delivery catheter for delivery of a second covered stent to be connected to a first covered stent comprising:
   a delivery lumen with a distal orifice configured for delivery and deployment of said second covered stent through said lumen at a target site of a side branch of said first covered stent, wherein a distal end of said delivery lumen is pre-bent to conform to a shape of said side branch of said first covered stent, wherein said first covered stent comprises a guiding element, and said guiding element is distally attached to a connection point at said side branch;

a longitudinal recess forming a slit in a wall of said delivery lumen; said longitudinal recess being configured to catch the guiding element into the longitudinal recess such that said distal end of said delivery lumen extends distally beyond said connection point when said guiding element is positioned through said delivery lumen and said longitudinal recess; and a guiding mate through which said guiding element is configured to be further positioned, such that said catheter is configured to slide along said guiding element to an orifice of said side branch, wherein said guiding mate has a distal end positioned proximally at a distance from said distal orifice of said delivery lumen such that said delivery lumen extends beyond said connection point when said distal end of said guiding mate is positioned adjacent to said connection point, wherein said connection point limits said guiding mate from further distal advancement beyond said connection point while allowing said delivery lumen of said catheter to extend beyond said connection point with said pre-bent distal end of said delivery lumen to extend into said side branch beyond said connection point during a delivery procedure of said second covered stent through said lumen.

2. The catheter according to claim 1, wherein the catheter is a multi-lumen catheter and said guiding mate is a first lumen different from said delivery lumen of said catheter for delivery of said second covered stent, and said first lumen has a distal opening which is arranged at the catheter at a distance proximal of a distal opening of said delivery lumen.

3. The catheter of claim 2, wherein a sheath surrounding said delivery lumen of said catheter is bent at least along a portion of said distance.

4. The catheter of claim 2 with said guiding element arranged through said guiding mate for delivery of said second stent graft through said delivery catheter to said target site of said branch, said second stent graft preferably being an extension stent graft.

* * * * *